United States Patent
Goetz et al.

(10) Patent No.: US 10,407,420 B2
(45) Date of Patent: Sep. 10, 2019

(54) IMIDAZOLE AND THIAZOLE COMPOSITIONS FOR MODIFYING BIOLOGICAL SIGNALING

(71) Applicant: Ohio University, Athens, OH (US)

(72) Inventors: Douglas Goetz, Athens, OH (US); Stephen C. Bergmeier, Athens, OH (US); Mark C. McMills, Athens, OH (US); Cina M. Orac, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 15/975,321

(22) Filed: May 9, 2018

(65) Prior Publication Data

US 2018/0362521 A1     Dec. 20, 2018

Related U.S. Application Data

(63) Continuation of application No. 15/326,821, filed as application No. PCT/US2015/029487 on May 6, 2015, now Pat. No. 10,023,567.

(Continued)

(51) Int. Cl.

| | | |
|---|---|---|
| C07D 417/14 | (2006.01) |
| C07D 233/84 | (2006.01) |
| C07D 277/16 | (2006.01) |
| C07D 277/36 | (2006.01) |
| C07D 277/84 | (2006.01) |
| C07D 405/04 | (2006.01) |
| C07D 413/04 | (2006.01) |
| C07D 417/06 | (2006.01) |
| A61K 31/4166 | (2006.01) |
| A61K 31/427 | (2006.01) |
| A61K 31/428 | (2006.01) |
| A61K 31/155 | (2006.01) |

(Continued)

(52) U.S. Cl.
CPC .......... *C07D 417/14* (2013.01); *A61K 31/155* (2013.01); *A61K 31/4166* (2013.01); *A61K 31/427* (2013.01); *A61K 31/428* (2013.01); *A61K 31/4439* (2013.01); *A61K 45/06* (2013.01); *C07D 233/84* (2013.01); *C07D 277/16* (2013.01); *C07D 277/36* (2013.01); *C07D 277/84* (2013.01); *C07D 405/04* (2013.01); *C07D 413/04* (2013.01); *C07D 417/04* (2013.01); *C07D 417/06* (2013.01); *Y02A 50/411* (2018.01)

(58) Field of Classification Search
CPC combination set(s) only.
See application file for complete search history.

(56) References Cited

U.S. PATENT DOCUMENTS

| | | |
|---|---|---|
| 4,129,656 A | 12/1978 | Lang et al. |
| 4,182,769 A | 1/1980 | Cherkofsky et al. |

(Continued)

FOREIGN PATENT DOCUMENTS

| | | |
|---|---|---|
| DE | 2459120 A1 | 6/1975 |
| FR | 6751 M | 3/1969 |

(Continued)

OTHER PUBLICATIONS

Matosiuk, D., "Synthesis and CNS activity of 1-alkyl-5-arylimidazolidine-2-thiones." Die Pharmazie 52.1 (1997): 71.*

(Continued)

*Primary Examiner* — John M Mauro
(74) *Attorney, Agent, or Firm* — Dinsmore & Shohl, LLP

(57) ABSTRACT

Compounds having General Formula (I) or General Formula (II):

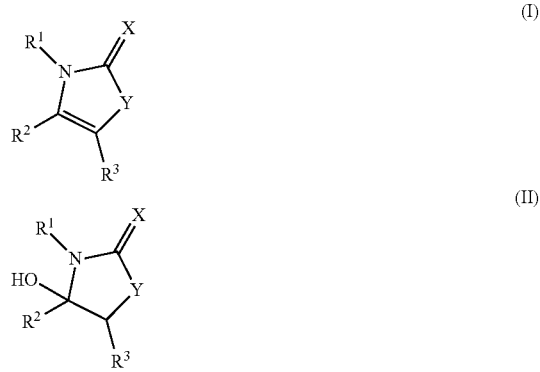

in which $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aromatic moieties, substituted aromatic moieties, heteroaromatic moieties, substituted heteroaromatic moieties, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof, and wherein the aliphatic or heteroaliphatic groups are optionally bonded to $R^2$ to form a ring; X is S or O; and Y is S or NH, may be used in pharmaceutical compositions that modify of biological signaling processes or as reagents for biological assays.

14 Claims, No Drawings

Related U.S. Application Data

(60) Provisional application No. 62/026,234, filed on Jul. 18, 2014, provisional application No. 62/026,164, filed on Jul. 18, 2014, provisional application No. 62/026,197, filed on Jul. 18, 2014.

(51) Int. Cl.
*A61K 31/4439* (2006.01)
*A61K 45/06* (2006.01)
*C07D 417/04* (2006.01)

(56) References Cited

U.S. PATENT DOCUMENTS

| | | | |
|---|---|---|---|
| 4,636,516 | A | 1/1987 | Kubo et al. |
| 6,365,616 | B1 | 4/2002 | Kohn et al. |
| 7,928,132 | B2 | 4/2011 | Kohn et al. |
| 2005/0277678 | A1 | 12/2005 | Lohray et al. |
| 2006/0211752 | A1 | 9/2006 | Kohn et al. |
| 2010/0004304 | A1 | 1/2010 | Kohn et al. |
| 2012/0136035 | A1 | 5/2012 | Gil |
| 2012/0283303 | A1 | 11/2012 | Pannecouque et al. |

FOREIGN PATENT DOCUMENTS

| | | | | |
|---|---|---|---|---|
| GB | 1155580 | A | * 6/1969 | ........... C07C 331/20 |
| WO | 2005118574 | A1 | 12/2005 | |
| WO | 2006019962 | A1 | 2/2006 | |
| WO | 2009049018 | A1 | 4/2009 | |

OTHER PUBLICATIONS

Safaei-Ghomi et al. The reaction of carbon disulfide with bromoacetophenone in the presence of primary amines: synthesis of 3-alkyl-4-phenyl-1,3-thiazole=2(3H)-thione derivatives. J. Sulfur Chem. 33(1): 87-92, 2012.
Belfort et al. A Placebo-Controlled Trial of Pioglitazone in Subjects with Nonalcoholic Steatohepatitis. N. Engl. J. Med. 355(22): 2297-2307, 2006.
PubChem, Compound Summary for CID 19897000, Dec. 5, 2007.
Emami et al. Synthesis and Evaluation of 2(3H)-Thiazole Thiones as Tyrosinase Inhibitors. Arch. Pharm. Chem: Life Sci. 345(8); 629-637, 2012.
Hozien, Zeinab A.: "Intramolecular Mannich reaction for synthesis of imidazo-[2,1-b]-1,3,5-thiadiazines and 1,2,4-trlazino[3,2,-b]-1,3,5-thiadiazines", Journal of Chemical Research, Synopses , (3), 99, 401-416.
Kinugawa, Jiro et al: "Fungicides VIII. Synthesis and antifungal activity of some thiocyanatolmidazoles, thlocyanatotriazoles, and 1-(4-thlocyanatophenyl)pyrazoles", Chemical & Pharmaceutical Bulletin , 12(4), 433-40.
Harii N et al: "Thyrocytes express a functional toll-like receptor 3: Over expressin can be induced by viral Infection and reversed by phenylmethimazole and is associated with Hashimoto's autoimmune thyroiditis", Molecular Endocrinology, The Endocrine Society, US, vol. 19, No. 5, Jan. 20, 2005 (Jan. 20, 2005), pp. 1231-1250.
Safaei-Ghomi Javad et al: "The reaction of carbon disulphide with[alpha]-haloketones and primary amines in the presence of potassium Iodide as cata", Journal of Chemical Sciences, Springer India, in Co-Publication with Indian Academy of Sciences, India, vol. 125, No. 5, Oct. 19, 2013 (Oct. 19, 2013), pp. 1087.1092.
Zsolnai, Tibor: "Antimicrobial activity of potential isothiocyanate formers. V.", Arzneimittel-Forschung , 19 (4), 558-72, 1969.
Database CA [Online] Chemical Abstracts Service, Columbus, Ohio, US; Usui, Yoshiro: "Fungicides . XIX. Syntheses of 3-aminothiazoline-2-thlone and 4H-1,3,4-thiadiazine derivatives", retrieved from STN Database accession No. 1969:461352.
Theoclitou, et al.; "Rapid Parallel Synthesis of Combinatorial Libraries of Substituted 3-Thio-1,2,4-triazoles and 2-Thioimidazoles"; J. Comb. Chem. 2002, 4, pp. 315-319.
International Search Report and Written Opinion dated Oct. 26, 2015 in reference to International Patent Application No. PCT/US2015/029460 filed May 6, 2015.
USPTO Restriction Requirement dated Jun. 9, 2017 in reference to co-pending U.S. Appl. No. 15/326,771, filed Jan. 17, 2017.
International Search Report and Written Opinion dated Jul. 22, 2015 in reference to International Patent Application No. PCT/US2015/029505 filed May 6, 2015.
International Search Report and Written Opinion dated Feb. 23, 2016 in reference to International Patent Application No. PCT/US2015/029487 filed May 6, 2015.
USPTO Office Action dated Jan. 8, 2018 in reference to co-pending U.S. Appl. No. 15/326,771, filed Jan. 17, 2017.
USPTO Non-Final Office Action dated Feb. 9, 2018 in reference to co-pending U.S. Appl. No. 15/326,782, filed Jan. 17, 2017.
Hassanabadi, A., "Three-component and one-pot reaction between phenacyl bromide and primary amines in the presence of carbon disulfide." Journal of Chemical Research 37.2 (2013): 71-72.
CAS Registry Number Compounds excerpted from JMM1 STN SRNTS Sep. 9, 2017; p. 1-4.
Ito, N., "A medium-term rat liver bioassay for rapid in vivo detection of carcinogenic potential of chemicals." Cancer Science 94.1 (2003): 3-8.
Non-Final Office Action dated Jul. 16, 2018 in reference to co-pending U.S. Appl. No. 15/326,782, filed Jan. 17, 2017.

* cited by examiner

IMIDAZOLE AND THIAZOLE COMPOSITIONS FOR MODIFYING BIOLOGICAL SIGNALING

CROSS-REFERENCE TO RELATED APPLICATIONS

This application is a continuation of U.S. patent application Ser. No. 15/326,821 filed Jan. 17, 2017; which is a national-stage entry of International Patent Application No. PCT/US2015/029487, filed May 6, 2015, which international application designates the United States and claims the benefit of U.S. Provisional Application Ser. No. 62/026,234, filed Jul. 18, 2014, of U.S. Provisional Application Ser. No. 62/026,164, filed Jul. 18, 2014, and of U.S. Provisional Application Ser. No. 62/026,197, filed Jul. 18, 2014.

TECHNICAL FIELD

The present specification relates generally to imidazole and thiazole compounds and, more specifically, to a class of imidazole 2-thiones, imidazole 2-ones, thiazole 2-thiones, and thiazole 2-ones that may modify various biological signaling processes.

BACKGROUND

The molecular mechanisms of normal physiology and pathology often involve a network of biologically active molecules that interact, in part, via intertwined signaling processes. To unravel these complex mechanisms, reagents are needed that modify signaling processes. Among a variety of uses, such compounds (i) will find use in probing the molecular mechanisms of normal and abnormal cellular processes; (ii) will find use in probing the molecular mechanisms of normal physiology and pathology; (iii) can become therapeutics, either alone or in combination with other drugs, for a host of animal and plant pathologies; (iv) can become reagents to engender normal physiology; (v) can be used as antimicrobials or antifungals; (vi) can become a reagent used to aid the processing of valuable products from biological sources; and (vii) can become a component of a diagnostic or prognostic assay.

DETAILED DESCRIPTION

Definitions

As used herein, the term "aliphatic" includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" may be used to indicate alkyl groups (substituted, unsubstituted, branched or unbranched) having from 1 to 6 carbon atoms.

In certain embodiments, the alkyl, alkenyl, and alkynyl groups described herein contain from 1 to 10 aliphatic carbon atoms. In other embodiments, the alkyl, alkenyl, and alkynyl groups described herein contain from 1 to 8 aliphatic carbon atoms. In still other embodiments, the alkyl, alkenyl, and alkynyl groups described herein contain from 1 to 6 aliphatic carbon atoms. In yet other embodiments, the alkyl, alkenyl, and alkynyl groups described herein contain from 1 to 4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which optionally may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

As used herein, the term "alicyclic" refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norbornyl moieties and the like, which optionally may bear one or more substituents.

As used herein, the term "alkoxy" or "alkyloxy" refers to a saturated (i.e., O-alkyl) or unsaturated (i.e., O-alkenyl and O-alkynyl) group attached to the parent molecular moiety through an oxygen atom. In certain embodiments, the alkyl group contains from 1 to 10 aliphatic carbon atoms. In yet other embodiments, the alkyl group contains from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

As used herein, the term "thioalkyl" refers to a saturated (i.e., S-alkyl) or unsaturated (i.e., S-alkenyl and S-alkynyl) group attached to the parent molecular moiety through a sulfur atom. In certain embodiments, the alkyl group contains from 1 to 10 aliphatic carbon atoms. In yet other embodiments, the alkyl group contains from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains from 1 to 10 aliphatic carbon atoms. In yet other embodiments, the alkyl groups contain from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of alkylamino include, but are not limited to, methylamino, ethylamino, isopropylamino and the like.

Some examples of substituents of the above-described aliphatic (and other) moieties of compounds described herein include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)$_2$R$^X$; —NR$^X$(CO)R$^X$, wherein each occurrence of R$^X$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above herein and may be substituted or unsubstituted, branched or unbranched, saturated or unsaturated, and wherein any of the aryl or heteroaryl substituents described above herein may be substituted or unsubstituted. Additional examples of generally applicable substituents are illustrated by the specific embodiments shown in the Examples that are described below.

In general, the term "aromatic moiety" as used herein refers to a stable monocyclic or polycyclic, unsaturated moiety having preferably from 3 to 14 carbon atoms, each of which may be substituted or unsubstituted. In certain embodiments, the terms "aromatic moiety" refer to a planar ring having p-orbitals perpendicular to the plane of the ring at each ring atom and satisfying the Hückel rule where the number of pi electrons in the ring is (4n+2), where n is an integer. A monocyclic or polycyclic, unsaturated moiety that does not satisfy one or all of these criteria for aromaticity is defined herein as "non-aromatic" and is encompassed by the term "alicyclic."

In general, the term "heteroaromatic moiety" as used herein refers to a stable monocyclic or polycyclic, unsaturated moiety having preferably from 3 to 14 carbon atoms, each of which may be substituted or unsubstituted; and comprising at least one heteroatom selected from O, S, and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Hückel rule where the number of pi electrons in the ring is (4n+2), where n is an integer.

It should be appreciated that aromatic and heteroaromatic moieties, as defined herein may be attached via an alkyl or heteroalkyl moiety and thus also include, as non-limiting examples: -(alkyl)-aromatic, -(heteroalkyl)-aromatic, -(heteroalkyl)-heteroaromatic, and -(heteroalkyl)-heteroaromatic moieties. Thus, as used herein, the phrases "aromatic or heteroaromatic moieties" and "aromatic, heteroaromatic, -(alkyl)-aromatic, -(heteroalkyl)-aromatic, -(heteroalkyl)-heteroaromatic, and -(heteroalkyl)-heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

As used herein, the term "aryl" does not differ significantly from the common meaning of the term in the art, and refers to an unsaturated cyclic moiety comprising at least one aromatic ring. In certain embodiments, "aryl" refers to a monocyclic or bicyclic carbocyclic ring system having one or two aromatic rings including, but not limited to, phenyl, naphthyl, tetrahydronaphthyl, indanyl, indenyl and the like.

As used herein, the term "heteroaryl" does not differ significantly from the common meaning of the term in the art, and refers to a cyclic aromatic radical having from 5 to 10 ring atoms of which one ring atom is selected from S, O, and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It should be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4-membered, 5-membered, 6-membered, or 7-membered substituted or unsubstituted alicyclic or heterocyclic moiety. Additional examples of generally applicable substituents are illustrated by the specific embodiments shown in the Examples that are described herein.

As used herein, the term "cycloalkyl" refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

As used herein, the term "heteroaliphatic" refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

As used herein, the term "heterocycloalkyl," "heterocycle," or "heterocyclic" refers to compounds that combine the properties of heteroaliphatic and cyclic compounds and include, but are not limited to, saturated and unsaturated mono- or polycyclic cyclic ring systems having from 5 to 16 atoms, wherein at least one ring atom is a heteroatom selected from O, S, and N (wherein the nitrogen and sulfur heteroatoms may optionally be oxidized), wherein the ring systems are optionally substituted with one or more functional groups, as defined herein. In certain embodiments, the term "heterocycloalkyl", "heterocycle" or "heterocyclic" refers to a non-aromatic 5-membered, 6-membered, or 7-membered ring or a polycyclic group wherein at least one ring atom is a heteroatom selected from O, S, and N (wherein the nitrogen and sulfur heteroatoms may optionally be oxidized), including, but not limited to, a bicyclic or tricyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds; (ii) the nitrogen and sulfur heteroatoms may optionally be oxidized; (iii) the nitrogen heteroatom may optionally be quaternized; and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof.

In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with groups including but not limited to aliphatic; alicyclic; heteroaliphatic; heterocyclic; aromatic; hetero aromatic; aryl; heteroaryl; alkylaryl; heteroalkylaryl; alkylheteroaryl; hetero alkylhetero aryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it should be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

As used herein, the terms "halo" and "halogen" refer to an atom selected from fluorine, chlorine, bromine and iodine.

As used herein, the term "haloalkyl" denotes an alkyl group, as defined above, having one, two, or three halogen atoms attached thereto and is exemplified by such groups as chloromethyl, bromoethyl, trifluoromethyl, and the like.

As used herein, the term "amino" refers to a primary amine (—NH$_2$), a secondary amine (—NHR$^X$), a tertiary amine (—NR$^X$R$^Y$), or a quaternary amine (—N$^+$R$^X$R$^Y$R$^Z$), where R$^X$, R$^Y$, and R$^Z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethyl amino, diethylaminocarbonyl, methylethylamino, isopropylamino, piperidino, trimethylamino, and propylamino.

As used herein, the term "$C_1$-$C_6$ alkylidene" refers to a substituted or unsubstituted, linear or branched, saturated divalent radical consisting solely of carbon and hydrogen atoms, having from one to six carbon atoms, having a free valence "-" at both ends of the radical.

As used herein, the term "$C_2$-$C_6$ alkenylidene" refers to a substituted or unsubstituted, linear or branched, unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic," "heteroaliphatic," "alkyl," "alkenyl," "alkynyl," "heteroalkyl," "heteroalkenyl," "heteroalkynyl," and the like encompass substituted and unsubstituted, saturated and unsaturated, and linear and branched groups. Similarly, the terms "alicyclic," "heterocyclic," "heterocycloalkyl," "heterocycle" and the like encompass substituted and unsubstituted, and saturated and unsaturated groups. Additionally, the tetras "cycloalkyl," "cycloalkenyl," "cycloalkynyl," "heterocycloalkyl," "heterocycloalkenyl," "heterocycloalkynyl," "aromatic," "heteroaromatic," "aryl," "heteroaryl" and the like encompass both substituted and unsubstituted groups.

The term "ameliorate" or "amelioration" means a lessening of the detrimental effect or severity of the disorder in the subject receiving therapy, the severity of the response being determined by means that are well known in the art.

The term "administration" of the pharmaceutically active compounds and the pharmaceutical compositions defined herein includes systemic use, as by injection (especially parenterally), intravenous infusion, suppositories and oral administration thereof, as well as topical application of the compounds and compositions. Oral administration is particularly preferred in embodiments herein.

As used herein, the term "comprising" means that various other compatible drugs and medicaments, as well as inert ingredients, can be conjointly employed in the pharmaceutical compositions and methods described herein, as long as the defined pharmaceutically active compounds and carriers are used in the manner disclosed. The term "comprising" thus encompasses and includes the more restrictive terms "consisting of" and "consisting essentially of."

As used herein, the term "compatible" with regard to components of a composition means that components of the composition are capable of being comingled without interacting in a manner which would substantially decrease the efficacy of the pharmaceutically active compound under ordinary use conditions.

The term "patient", as used herein, is intended to encompass any mammal, animal or human subject, which may benefit from treatment with the compounds, compositions and methods described herein, and includes children and adults.

"Pharmaceutically-acceptable" shall mean that the pharmaceutically active compound and other ingredients used in the pharmaceutical compositions and methods defined herein are suitable for use in contact with the tissues of humans and lower animals without undue toxicity, irritation, allergic response, and the like, commensurate with a reasonable benefit/risk ratio.

As used herein, the term "pharmaceutical carrier" denotes a solid or liquid filler, diluent or encapsulating substance. These materials are well known to those skilled in the pharmaceutical arts. Some examples of the substances that can serve as pharmaceutical carriers include sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants, such as sodium lauryl sulfate, as well as coloring agents, flavoring agents, tableting agents, and preservatives, can also be present. Formulation of the components into pharmaceutical compositions is done using conventional techniques.

The term "pharmaceutically acceptable salts" refers to salts prepared from pharmaceutically acceptable non-toxic bases or acids including inorganic or organic bases and inorganic or organic acids. Salts derived from inorganic bases include: aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include: salts of primary, secondary, and tertiary amines, substituted amines including naturally occurring substituted amines, cyclic amines, and basic ion exchange resins, such as arginine, betaine, caffeine, choline, N,N'-dibenzyl ethylenediamine, diethylamine, 2-diethyl aminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When a compound is basic, salts may be prepared from pharmaceutically acceptable non-toxic acids, including inorganic and organic acids. Such acids include: acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. Thus, representative pharmaceutically acceptable salts include but are not limited to acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexyl-resorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. It will be understood that, as used herein, the compounds referred to herein are meant to also include the pharmaceutically acceptable salts.

It is understood that certain embodiments herein encompass the use of pharmaceutically acceptable salts, pharmaceutically acceptable solvates, or pharmaceutically acceptable salts solvated with pharmaceutically acceptable solvents. As used herein, the term "solvate" or "salt solvated" refers to a complex of variable stoichiometry formed by a solute (such as compounds of Formula (I) or (II)

described below (or a salt thereof)) and a solvent. In some embodiments, such solvents do not interfere with the biological activity of the solute. Examples of suitable solvents include, but are not limited to, water, methanol, ethanol and acetic acid. In illustrative embodiments, the solvent is a pharmaceutically acceptable solvent. Examples of suitable pharmaceutically acceptable solvents include, without limitation, water, ethanol, and acetic acid. In one particular embodiment, the solvent is water, providing a "hydrate."

The term "prodrug" indicates a therapeutic agent that is prepared in an inactive form that is converted to an active form (i.e., drug) within the body or cells thereof by the action of endogenous enzymes or other chemicals and/or conditions.

The phrase "safe and effective amount" means a sufficient amount of pharmaceutically active compound to desirably affect the treatment of autoimmune diseases or to suppress the rejection of transplanted tissue, at a reasonable benefit/risk ratio attendant with any medical treatment. In one embodiment, a "safe and effective amount" means a sufficient amount of a pharmaceutically active compound to inhibit lipopolysaccharide (LPS) induction of IL-6, INF-β, and/or iNOS. Within the scope of sound medical judgement, the required dosage of a pharmaceutically active agent or of the pharmaceutical composition containing that active agent will vary with the severity of the condition being treated, the duration of the treatment, the nature of adjunct treatment, the age and physical condition of the patient, the specific active compound employed, and like considerations discussed more fully hereinafter. In this regard it should be noted that the use of certain compounds herein at high doses can induce side effects, such as aplastic anemia, agranulocytosis, hepatic dysfunction and dermatitis, in certain patients. In arriving at the "safe and effective amount" for a particular compound, these risks must be taken into consideration, as well as the fact that the compounds described herein may provide pharmaceutical activity at lower dosage levels than conventional methimazole compounds.

"Therapeutic agent" as used herein refers to those agents effective in the prevention or treatment of a disorder or pathologic physiological condition. Therapeutic agent includes the pro-drugs and pharmaceutical derivatives thereof including but not limited to the corresponding nitrosated and/or nitrosylated derivatives.

"Therapeutically effective amount" refers to the amount of the compound and/or composition that is effective to achieve its intended purpose.

"Toll-like receptors" or "TLRs" are type I transmembrane proteins containing repeated leucine-rich motifs in their extracellular domains and a cytoplasmic tail that contains a conserved region called the Toll/IL1 receptor (TIR) domain. At least 10 mammalian TLR proteins have been identified, Toll-like receptors 1-10. TLRs play a critical role in early innate immunity to invading pathogens by sensing microorganisms or noxious environmental agents. These evolutionarily conserved receptors, homologues of the Drosophila Toll gene, recognize highly conserved structural motifs expressed by microbial pathogens, called pathogen-associated microbial patterns (PAMPs) and sense products of tissue damage by noxious agents or tissue injury, for example dsRNA. PAMPs include various bacterial cell wall components such as lipopolysaccharide (LPS), peptidoglycan (PGN) and lipopeptides, as well as flagellin, bacterial DNA and viral double-stranded RNA. TLR thus protect mammals from pathogenic organisms, such as viruses, bacteria, parasitic agents, or fungi, and from tissue injury, by generating an "innate immune" response to products of the pathogenic organism. They thus may additionally protect animals from noxious environmental agents that destroy cells and release dsRNA or other PAMPs that can interact with the TLR. The innate immune response results in increases in genes encoding several inflammatory cytokines, chemokines, as well as co-stimulatory molecules, and is critical for the development of antigen-specific adaptive immunity. Stimulation of TLRs by PAMPs initiates a signaling cascade that involves a number of proteins, such as MyD88 and IRAK1. This signaling cascade leads to the activation of the transcription factor NF-κB which induces the secretion of pro-inflammatory cytokines (such as TNF α and IL-1β) and effector cytokines that direct the adaptive immune response. The signaling cascade additionally involves adaptors such as TRIF/TICAM-1 which can signal the IRF-3 pathway to increase Type 1 IFN production, activate Stats, increase IRF-1 gene expression, and activate ISRE's, interferon response factor (IRF) elements. In the case of virus, injection of dsRNA or single strand RNA with its replication can activate viral kinases, bypass TLR, activate PKR and IRF-3, and initiate the NF-κB and Type 1 IFN cascades, which, by the autocrine/paracrine action of type 1 IFNs, the cytokines and the chemokines can initiate the innate immune-adaptive immune response sequence.

"Treat," "treating," "treatment," and "therapy" as used herein refer to any curative therapy, prophylactic therapy, ameliorative therapy and preventive therapy for a subject.

Compositions

Embodiments herein are directed to compositions and pharmaceutical compositions. The compositions and pharmaceutical compositions contain one or more compounds having General Formula (I) or General Formula (II):

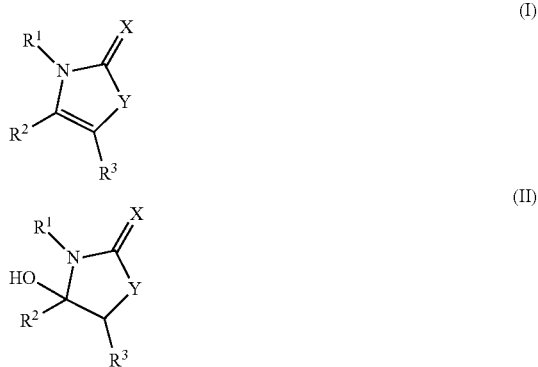

or pharmaceutically-acceptable salts or solvates thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH, with the proviso that when $R^2$ is phenyl, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof (b) $R^1$ is hexyl; or (c) $R^1$ is Ph(CH$_2$)$_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof. The compositions and pharmaceutical compositions containing one or more compounds of General Formula (I) and General Formula (II) may be used as a medicament, to inhibit LPS induction of IL-6 or NOS transcripts in biological signalling networks, as antimicrobial agents, as antifungal agents, or in diagnostic or prognostic biological assays, for example.

In the compounds of General Formula (I) and General Formula (II), group $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof. In illustrative non-limiting embodiments, group $R^1$ is chosen from methyl, ethyl, propyl, butyl, pentyl, hexyl, 2-propenyl,

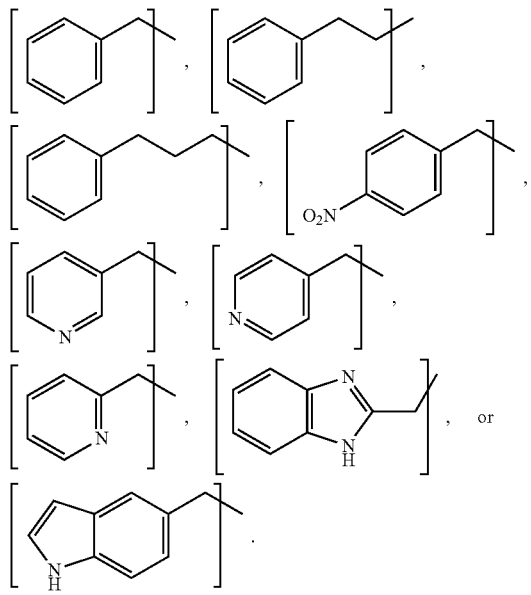

In other illustrative embodiments, group $R^1$ may be a group $Q^1$:

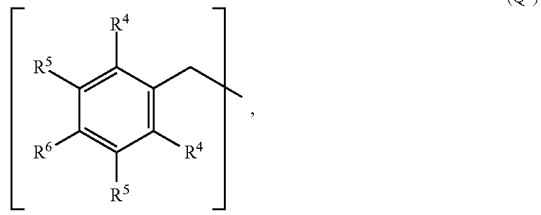

(Q$^1$)

in which groups $R^4$, $R^5$, and $R^6$ are independently chosen from —H, halo (such as —F, —Cl, or —Br), —NO$_2$, —CN, or alkylesters such as —OCH$_3$. In other illustrative embodiments, group $R^1$ may be a group $Q^1$, in which groups $R^4$ and $R^5$ all are H and group $R^6$ is chosen from alkylesters, Cl, —NO$_2$, or —CN.

In the compounds of General Formula (I) and General Formula (II), group $R^2$ is chosen from unsubstituted aryl groups, substituted aryl groups, heteroaryl groups, substituted heteroaryl groups, and coumarin. In some embodiments, group $R^2$ may be an unsubstituted phenyl group, a 2-monosubstituted phenyl group, a 3-monosubstituted phenyl group, a 4-monosubstituted phenyl group, a 2,3-disubstituted phenyl group, a 2,4-disubstituted phenyl group, a 2,5-disubstituted phenyl group, a 3,4-disubstituted phenyl group, or a 3,5-disubstituted phenyl group. In such embodiments, group $R^2$ may be a group $Q^2$:

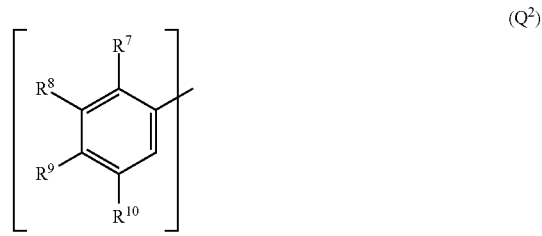

(Q$^2$)

In embodiments in which group $R^2$ is a monosubstituted phenyl group $Q^2$, in group $Q^2$ exactly three of any of $R^7$, $R^8$, $R^9$, and $R^{10}$ are hydrogen, and the one of $R^7$, $R^8$, $R^9$, and $R^{10}$ that is not hydrogen may be chosen from methoxy, ethoxy, hydroxy, trifluoromethoxy, methyl, trifluoromethyl, N-methylamino, (N,N)-dimethylamino, cyano, halo (for example, chloro, fluoro, or bromo), or nitro, for example.

In embodiments in which group $R^2$ is a disubstituted phenyl group $Q^2$, in group $Q^2$ exactly two of any of $R^7$, $R^8$, $R^9$, and $R^{10}$) are hydrogen, and the two groups of $R^7$, $R^8$, $R^9$, and $R^{10}$) that are not hydrogen may be independently chosen from methoxy, ethoxy, hydroxy, trifluoromethoxy, dimethylamino, cyano, chloro, fluoro, or nitro, for example.

In some embodiments in which group $R^2$ is a disubstituted phenyl group $Q^2$, group $Q^2$ may be any isomer of hydroxyphenyl, dihydroxyphenyl, methoxyphenyl, dimethoxyphenyl, halophenyl, dihalophenyl, chlorophenyl, dichlorophenyl, fluorophenyl, halohydroxyphenyl, halomethoxyphenyl, chlorohydroxylphenyl, chloromethoxyphenyl, fluorohydroxyphenyl, fluoromethoxyphenyl.

Illustrative, non-limiting examples of group $R^2$ as a monosubstituted phenyl group $Q^2$ or a disubstituted phenyl group $Q^2$ may include 2-methoxyphenyl; 3-methoxyphenyl; 3-chlorophenyl; 2,5-dimethoxyphenyl; 2,4-dimethoxyphenyl; 3,4-dimethoxyphenyl; 4-(dimethyl amino)phenyl; 4-(trifluoromethoxy)phenyl; 4-cyanophenyl; 3-hydroxyphenyl; 2,4-hydroxyphenyl; 3,4-dichlorophenyl; 3-nitrophenyl; 2-hydroxy-5-chlorophenyl; 2-methylphenyl; 2,5-dimethylphenyl; 2-methoxy-5-fluorophenyl; and 2-chloro-5-(trifluoromethyl)phenyl.

In other embodiments, group $R^2$ may be an aryl group such as, for example,

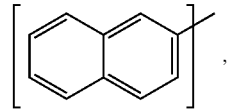

or a substituted derivative thereof. In other embodiment, group $R^2$ may be an aryl group other than phenyl. In other embodiments, group $R^2$ may be a heteroaryl group such as, for example,

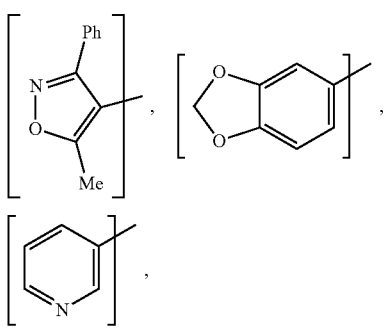

or substituted derivatives of any of these. In other embodiments, group $R^2$ may be coumarin, such as, for example,

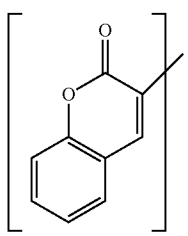

In some embodiments, preferred compounds of General Formula (I) and General Formula (II) may include compounds of formulas (IV)-(IX):

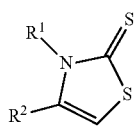 (IV)

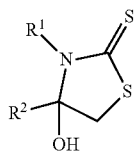 (V)

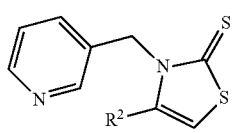 (VI)

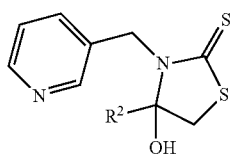 (VII)

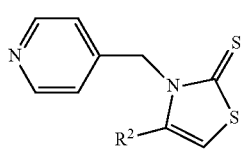 (VIII)

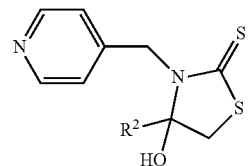 (IX)

in which groups $R^1$ and $R^2$ are as described above and groups $R^3$ of formulas (I) and (II) are hydrogen.

In some embodiments, preferred compounds of General Formula (I) and General Formula (II) may include compounds of formulas (VI) or (VII):

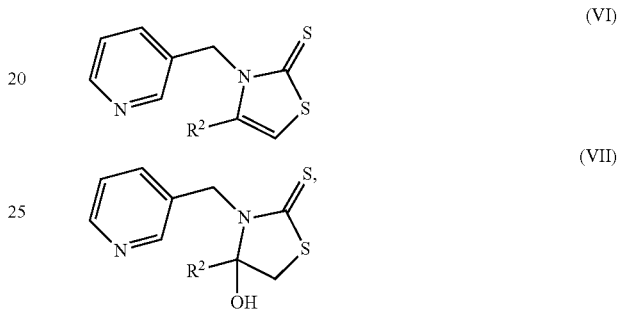

in which group $R^2$ is as described above.

In the compounds of General Formula (I) and General Formula (II), group $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof. In non-limiting exemplary embodiments, $R^3$ may be methyl, ethyl, n-propyl, isopropyl, butyl, 3-butenyl, phenyl, or 2-phenylethyl. In some embodiments, $R^3$ is hydrogen. The aliphatic or heteroaliphatic groups of $R^3$ optionally may be bonded to group $R^2$ to form a ring. One illustrative example of an aliphatic group $R^3$ bonded to group $R^2$ to form a ring is the structure

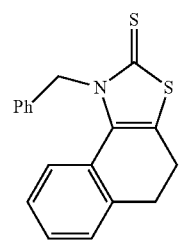 [SMILES: S=c1sc2c(n1Cc1ccccc1)-c1ccccc1CC2]

having General Formula (I), in which group $R^1$ attached to the nitrogen atom is phenylmethyl (benzyl), group $R^2$ is phenyl and group $R^3$ is an ethyl group bonded to the 2-position of the phenyl ring of $R^2$ to form a six-membered ring including all of group $R^3$ and part of group $R^2$.

In the compounds of General Formula (I) and General Formula (II), X is S or O; and Y is S or NH. Thus, in some embodiments, group X is S and group Y is S. In other embodiments, group X is S and group Y is NH. In other embodiments, group X is O and group Y is S. In other embodiments, group X is O and group Y is NH.

The compounds of General Formula (I) and General Formula (II) may be prepared using any suitable synthetic scheme. In one exemplary synthetic scheme, the compounds having General Formula (I) or General Formula (II) in which X=O or S and Y=NH may be synthesized by adding an isothiocyanate or isocyanate of formula (1a):

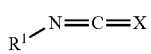

(1a)

(100 mol %, X=O or S) and Et₃N (50 mol. %) to an EtOH (0.01 M) solution of a hydrochloride of a methylamino ketone of formula (1b) (100 mol. %):

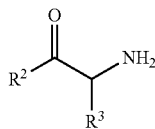

(1b)

to form a reaction mixture. The reaction mixture may be heated at a suitable reaction temperature for a suitable time. If the heating is accomplished using microwave irradiation, the rate of elimination of a hydroxyl group from the product is increased, so as to substantially favor formation of compounds of General Formula (I) over those of General Formula (II). Conversely, application of heat without microwave irradiation favors compounds of General Formula (II) as products. The solvent may be removed, and the product may be isolated by flash chromatography, for example.

Compounds having General Formula (II) in which X=S and Y=S may be synthesized by adding carbon disulfide (CS₂; 150 mol. %) and K₂CO₃ (50 mol. %) to a solution of an amine (150 mol. %) of the formula (2a):

(2a)

in H₂O:EtOH (0.2 M, 1:1) and then adding a 2-bromoketone derivative (100 mol %) of formula (2b):

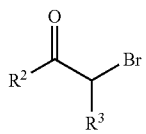

(2b)

to form a reaction mixture. After stirring, a crude reaction mixture may be extracted with a solvent such as ethyl acetate, and the combined organic layers may be dried and filtered. The solvent may be evaporated by rotary evaporation. The product may be isolated using a solvent such as 10%-20% EtOAc in hexanes. In some cases, some products may precipitate during the reaction. In such cases the product may be isolated by filtration, washed thoroughly with solvent, then dried.

Compounds having General Formula (II), where X=O and Y=S, may be synthesized by adding a solution of carbonyl sulfide (COS; 150 mol. %) and K₂CO₃ (50 mol. %) to a solution of an amine (150 mol. %) of the formula (2a):

R¹—NH₂ (2a)

in H₂O:EtOH (0.2 M, 1:1) and then adding a 2-bromoketone derivative (100 mol %) of formula (2b):

(2b)

to form a reaction mixture. After stirring, a crude reaction mixture may be extracted with a solvent such as ethyl acetate, and the combined organic layers may be dried and filtered. The solvent may be evaporated by rotary evaporation. The product may be isolated using a solvent such as 10%-20% EtOAc in hexanes. In some cases, some products may precipitate during the reaction. In such cases the product may be isolated by filtration, washed thoroughly with solvent, then dried.

Compounds having General Formula (I), in which X=O or S and Y=S, may be synthesized by dehydrating a compound having General Formula (II) prepared according by any suitable synthetic route, such as the route described above, for example, in which groups R¹, R², R³, X, and Y of the compound having General Formula (II) are the same as those in the desired compound having General Formula (I).

In TABLE 1, compounds having General Formula (I) or (II) according to various embodiments are provided, along with exemplary reactants for forming the compound having General Formula (I) or (II) according to the synthetic schemes described above and further described in the Examples section below:

TABLE 1

| Reference | Reactant (1a) or (2a) | Reactant (1b) or (2b) | Compound of General Formula (I) or (II) |
|---|---|---|---|
| COB-117 | (3-methoxyphenyl)-2-aminoethanone | H₃C-N=C=S | thione imidazole with 3-methoxyphenyl |

TABLE 1-continued

| Reference | Reactant (1a) or (2a) | Reactant (1b) or (2b) | Compound of General Formula (I) or (II) |
|---|---|---|---|
| COB-118 | 2-methoxyphenacylamine | methyl isothiocyanate | 1-methyl-5-(2-methoxyphenyl)-imidazole-2-thione |
| COB-119 | 3-chlorophenacylamine | methyl isothiocyanate | 1-methyl-5-(3-chlorophenyl)-imidazole-2-thione |
| COB-123 | 3,4-dimethoxyphenacylamine | methyl isothiocyanate | 1-methyl-5-(3,4-dimethoxyphenyl)-imidazole-2-thione |
| COB-124 | 3-methoxyphenacylamine | ethyl isocyanate | 1-ethyl-5-(3-methoxyphenyl)-imidazol-2-one |
| COB-125 | 3-chlorophenacylamine | ethyl isocyanate | 1-ethyl-5-(3-chlorophenyl)-imidazol-2-one |

TABLE 1-continued
| Reference | Reactant (1a) or (2a) | Reactant (1b) or (2b) | Compound of General Formula (I) or (II) |
| --- | --- | --- | --- |
| COB-126 | 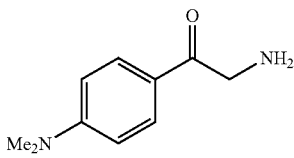 [SMILES: CN(C)c1ccc(C(=O)CN)cc1] | 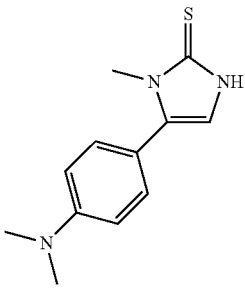 [SMILES: CN(C)c1ccc(-c2c[nH]c(=S)n2C)cc1] | 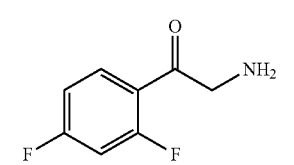 [SMILES: NCC(=O)c1ccc(F)cc1F] |
| COB-128 | 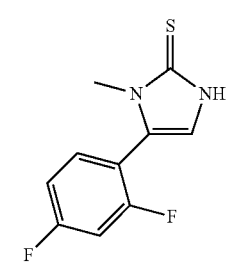 | H₃C—N=C=S | 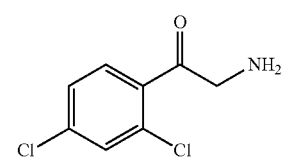 [SMILES: NCC(=O)c1ccc(Cl)cc1Cl] |
| COB-129 | 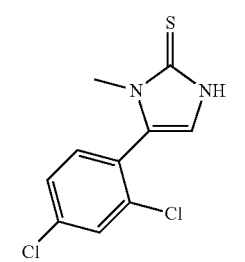 | H₃C—N=C=S | 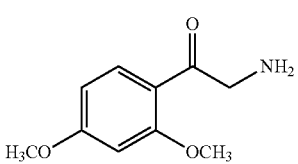 |
| COB-130 | 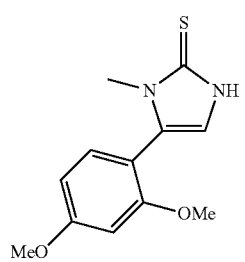 [SMILES: COc1ccc(-c2c[nH]c(=S)n2C)c(OC)c1] | H₃C—N=C=S | 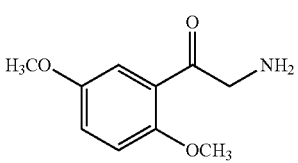 [SMILES: COc1ccc(OC)c(C(=O)CN)c1] |
| COB-132 | 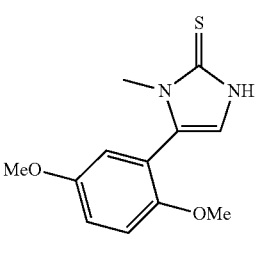 [SMILES: COc1ccc(OC)c(-c2c[nH]c(=S)n2C)c1] | H₃C—N=C=S | 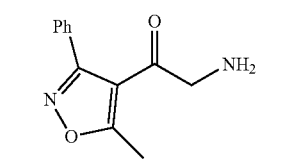 |
| COB-133 | 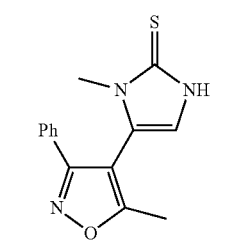 | H₃C—N=C=S |  |

TABLE 1-continued

| Reference | Reactant (1a) or (2a) | Reactant (1b) or (2b) | Compound of General Formula (I) or (II) |
| --- | --- | --- | --- |
| COB-134 | 2-amino-1-(4-trifluoromethoxyphenyl)ethanone | methyl isothiocyanate | 1-methyl-5-(4-trifluoromethoxyphenyl)-1H-imidazole-2(3H)-thione |
| COB-138 | 2-amino-1-(4-cyanophenyl)ethanone | methyl isothiocyanate | 4-(1-methyl-2-thioxo-2,3-dihydro-1H-imidazol-5-yl)benzonitrile |
| COB-139 | 2-amino-1-(naphthalen-2-yl)ethanone | methyl isothiocyanate | 1-methyl-5-(naphthalen-2-yl)-1H-imidazole-2(3H)-thione |
| COB-143 | 2-bromo-1-(2,5-dimethoxyphenyl)ethanone | benzylamine + CS₂ | 3-benzyl-4-(2,5-dimethoxyphenyl)-4-hydroxythiazolidine-2-thione |
| COB-144 | Dehydration of COB-143 | | 3-benzyl-4-(2,5-dimethoxyphenyl)-2,3-dihydrothiazole-2-thione |
| COB-146 | 2-amino-1-(benzo[d][1,3]dioxol-5-yl)ethanone | methyl isothiocyanate | 5-(benzo[d][1,3]dioxol-5-yl)-1-methyl-1H-imidazole-2(3H)-thione |

TABLE 1-continued

| Reference | Reactant (1a) or (2a) | Reactant (1b) or (2b) | Compound of General Formula (I) or (II) |
|---|---|---|---|
| COB-152 | PhC(O)CH$_2$Br | 3-pyridyl-CH$_2$NH$_2$ + CS$_2$ | 3-(pyridin-3-ylmethyl)-4-hydroxy-4-phenylthiazolidine-2-thione |
| COB-153 | Dehydration of COB-152 | | 3-(pyridin-3-ylmethyl)-4-phenyl-2,3-dihydrothiazole-2-thione |
| COB-161 | 2-bromo-1-tetralone | PhCH$_2$NH$_2$ | 1-benzyl-4,5-dihydronaphtho[1,2-d]thiazole-2(1H)-thione fused system |
| COB-168 | PhC(O)CH$_2$Br | PhCH$_2$CH$_2$CH$_2$NH$_2$ + CS$_2$ | 3-(3-phenylpropyl)-4-hydroxy-4-phenylthiazolidine-2-thione |
| COB-178 | Dehydration of COB-168 | | 3-(3-phenylpropyl)-4-phenyl-2,3-dihydrothiazole-2-thione |
| COB-176 | 3-pyridyl-C(O)CH$_2$Br | 3-pyridyl-CH$_2$NH$_2$ + CS$_2$ | 3-(pyridin-3-ylmethyl)-4-hydroxy-4-(pyridin-3-yl)thiazolidine-2-thione |
| COB-177 | Dehydration of reaction product of PhC(O)CH$_2$Br and PhCH$_2$CH$_2$NH$_2$ + CS$_2$ | | 3-(2-phenylethyl)-4-phenyl-2,3-dihydrothiazole-2-thione |

TABLE 1-continued
| Reference | Reactant (1a) or (2a) | Reactant (1b) or (2b) | Compound of General Formula (I) or (II) |
|---|---|---|---|
| COB-180 | 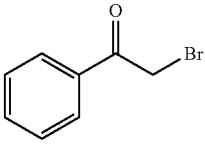 | 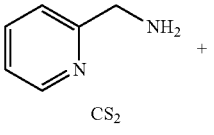 + CS₂ | 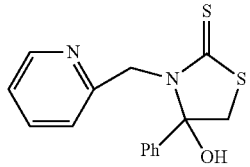 |
| COB-189 | Dehydration of COB-180 | | 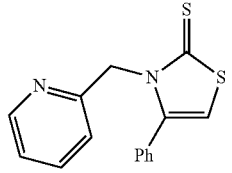 |
| COB-183 | 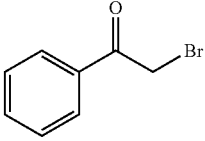 | 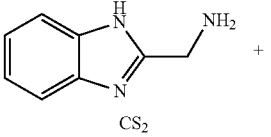 + CS₂ | 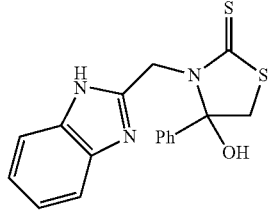 |
| COB-192 | Dehydration of COB-183 | | 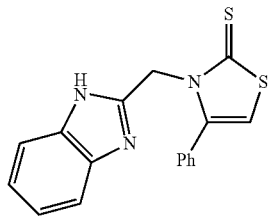 |
| COB-186 | 2× 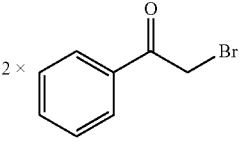 | 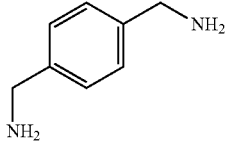 + CS₂ | 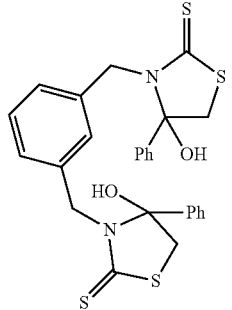 |
| COB-193 | Dehydration of COB-186 | | 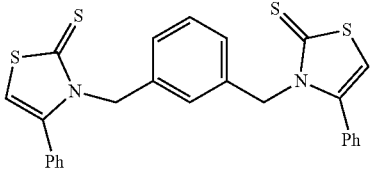 |
| COB-187 | 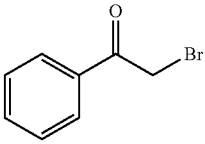 | 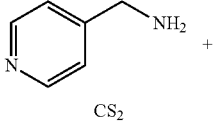 + CS₂ | 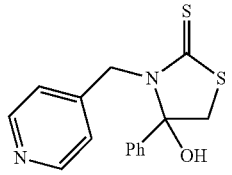 |

TABLE 1-continued

| Reference | Reactant (1a) or (2a) | Reactant (1b) or (2b) | Compound of General Formula (I) or (II) |
|---|---|---|---|
| COB-188 | phenacyl bromide | 1H-indol-5-ylmethanamine + CS₂ | 3-((1H-indol-5-yl)methyl)-4-hydroxy-4-phenylthiazolidine-2-thione |
| COB-190 | Dehydration of reaction product of phenacyl bromide and 4-chlorobenzylamine + CS₂ | | 3-(4-chlorobenzyl)-4-phenyl-2,3-dihydrothiazole-2-thione |
| COB-191 | Dehydration of reaction product of phenacyl bromide and 4-nitrobenzylamine + CS₂ | | 3-(4-nitrobenzyl)-4-phenyl-2,3-dihydrothiazole-2-thione |
| COB-196 | 2-bromo-1-(3-hydroxyphenyl)ethanone | benzylamine + CS₂ | 3-benzyl-4-(3-hydroxyphenyl)-4-hydroxythiazolidine-2-thione |
| COB-197 | 2-bromo-1-(2,5-dimethoxyphenyl)ethanone | pyridin-3-ylmethanamine + CS₂ | 4-(2,5-dimethoxyphenyl)-4-hydroxy-3-(pyridin-3-ylmethyl)thiazolidine-2-thione |
| COB-203 | Dehydration of COB-197 | | 4-(2,5-dimethoxyphenyl)-3-(pyridin-3-ylmethyl)-2,3-dihydrothiazole-2-thione |

TABLE 1-continued

| Reference | Reactant (1a) or (2a) | Reactant (1b) or (2b) | Compound of General Formula (I) or (II) |
|---|---|---|---|
| COB-198 | 3'-hydroxyphenacyl bromide | 3-(aminomethyl)pyridine + CS₂ | 3-(pyridin-3-ylmethyl)-4-(3-hydroxyphenyl)-4-hydroxythiazolidine-2-thione |
| COB-199 | 2',4'-dimethoxyphenacyl bromide | 3-(aminomethyl)pyridine + CS₂ | 3-(pyridin-3-ylmethyl)-4-(2,4-dimethoxyphenyl)-4-hydroxythiazolidine-2-thione |
| COB-204 | Dehydration of COB-199 | | 3-(pyridin-3-ylmethyl)-4-(2,4-dimethoxyphenyl)-2,3-dihydrothiazole-2-thione |
| COB-200 | 2',4'-dihydroxyphenacyl bromide | 3-(aminomethyl)pyridine + CS₂ | 3-(pyridin-3-ylmethyl)-4-(2,4-dihydroxyphenyl)-4-hydroxythiazolidine-2-thione |
| COB-201 | 4'-methoxyphenacyl bromide | 3-(aminomethyl)pyridine + CS₂ | 3-(pyridin-3-ylmethyl)-4-(4-methoxyphenyl)-4-hydroxythiazolidine-2-thione |

TABLE 1-continued

| Reference | Reactant (1a) or (2a) | Reactant (1b) or (2b) | Compound of General Formula (I) or (II) |
|---|---|---|---|
| COB-206 | Dehydration of COB-201 | | 3-(pyridin-3-ylmethyl)-4-(4-methoxyphenyl)-thiazole-2-thione |
| COB-202 | 3-(2-bromoacetyl)-2H-chromen-2-one | pyridin-3-ylmethanamine + CS₂ | 3-(pyridin-3-ylmethyl)-4-hydroxy-4-(2-oxo-2H-chromen-3-yl)-thiazolidine-2-thione |
| COB-205 | Dehydration of COB-202 | | 3-(pyridin-3-ylmethyl)-4-(2-oxo-2H-chromen-3-yl)-thiazole-2-thione |
| COB-207 | 1-(pyridin-3-yl)-2-bromoethanone | propylamine + CS₂ | 3-propyl-4-hydroxy-4-(pyridin-3-yl)-thiazolidine-2-thione |
| COB-214 | Dehydration of COB-207 | | 3-propyl-4-(pyridin-3-yl)-thiazole-2-thione |
| COB-208 | 4-(2-bromoacetyl)benzonitrile | propylamine + CS₂ | 3-propyl-4-hydroxy-4-(4-cyanophenyl)-thiazolidine-2-thione |

TABLE 1-continued

| Reference | Reactant (1a) or (2a) | Reactant (1b) or (2b) | Compound of General Formula (I) or (II) |
|---|---|---|---|
| COB-216 | Dehydration of COB-208 | | |
| COB-209 | | | |
| COB-210 | | | |
| COB-219 | Dehydration of COB-210 | | |
| COB-212 | | | |
| COB-213 | | | |

TABLE 1-continued
| Reference | Reactant (1a) or (2a) | Reactant (1b) or (2b) | Compound of General Formula (I) or (II) |
|---|---|---|---|
| COB-220 | Dehydration of COB-213 | | 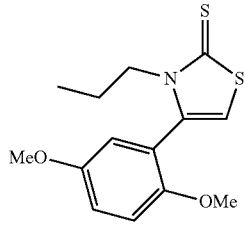 |
| COB-215 | Dehydration of reaction product of 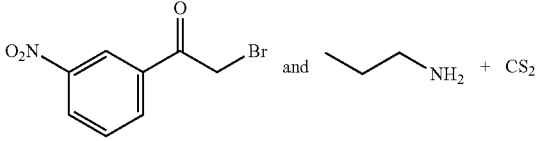 and 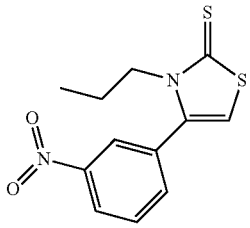 + CS₂ | | 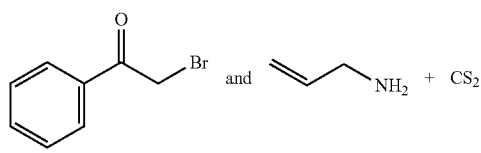 |
| COB-217 | Dehydration of reaction product of 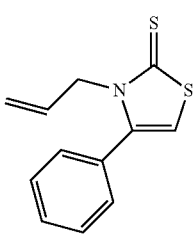 and 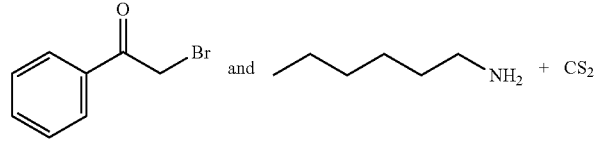 + CS₂ | | 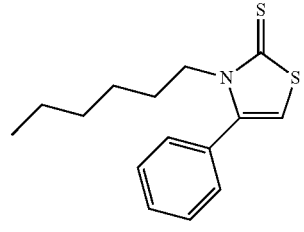 |
| COB-218 | Dehydration of reaction product of 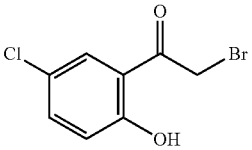 and 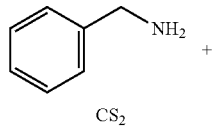 + CS₂ | | 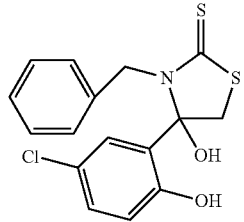 |
| COB-221 | 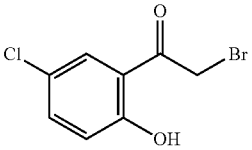 | 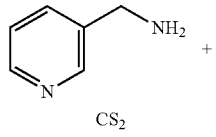 + CS₂ | 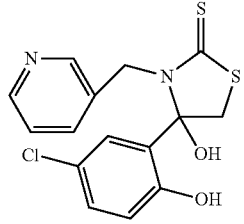 |
| COB-222 | | | |

TABLE 1-continued
| Reference | Reactant (1a) or (2a) | Reactant (1b) or (2b) | Compound of General Formula (I) or (II) |
|---|---|---|---|
| COB-223 | 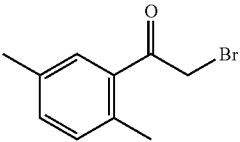 | 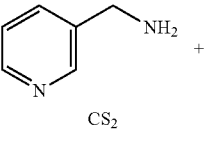 + CS₂ | 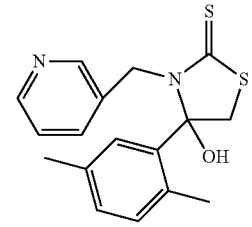 |
| COB-224 | 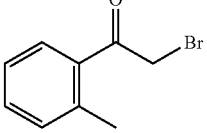 | 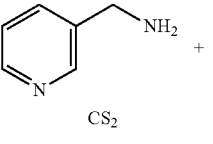 + CS₂ | 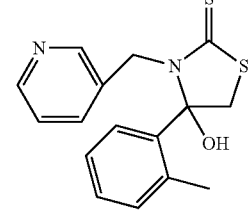 |
| COB-225 | 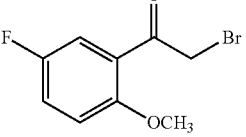 | 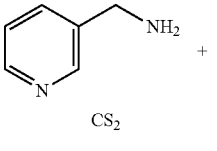 + CS₂ | 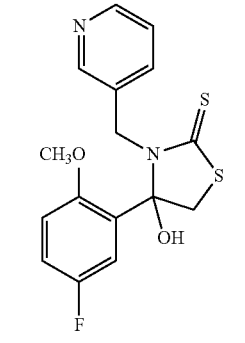 |
| COB-226 | 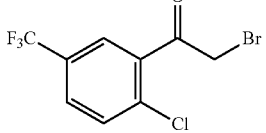 | 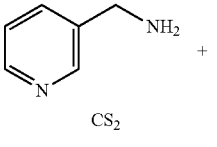 + CS₂ | 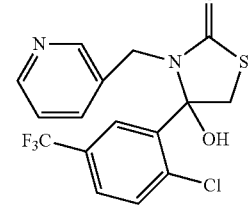 |
| DRB-3 | Dehydration of reaction product of: 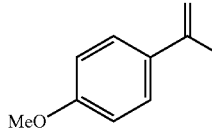 and  + CS₂ | |  |
| GWB-93 | Dehydration of reaction product of: 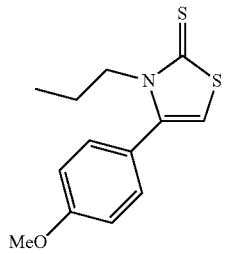 and CH₃NH₂ + CS₂ | | 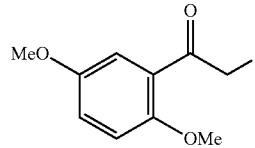 |

TABLE 1-continued

| Reference | Reactant (1a) or (2a) | Reactant (1b) or (2b) | Compound of General Formula (I) or (II) |
|---|---|---|---|
| Z-01 | Dehydration of reaction product of: 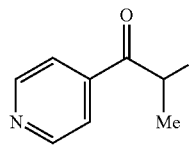 and CH₃NH₂ + CS₂ | | 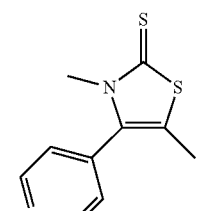 |
| Z-02 | Dehydration of reaction product of: 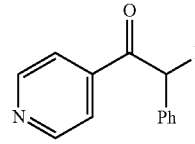 and CH₃NH₂ + CS₂ | | 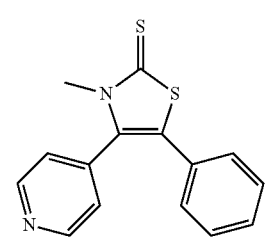 |
| Z-03 | Dehydration of reaction product of: 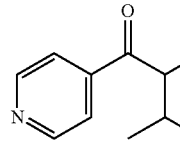 and CH₃NH₂ + CS₂ | | 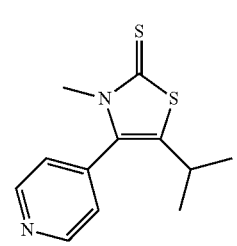 |
| Z-04 | Dehydration of reaction product of: 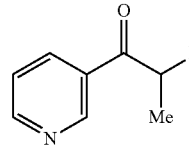 and CH₃NH₂ + CS₂ | | 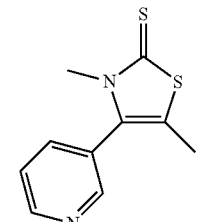 |
| Z-05 | Dehydration of reaction product of: 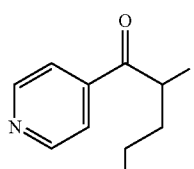 and CH₃NH₂ + CS₂ | | 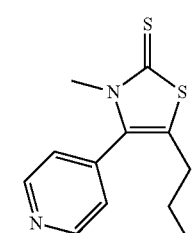 |
| Z-06 | Dehydration of reaction product of: 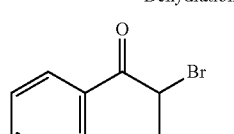 and 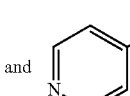 + CS₂ | | 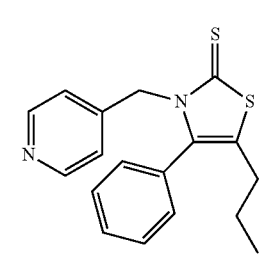 |

TABLE 1-continued

| Reference | Reactant (1a) or (2a) | Reactant (1b) or (2b) | Compound of General Formula (I) or (II) |
|---|---|---|---|
| Z-07 | Dehydration of reaction product of: 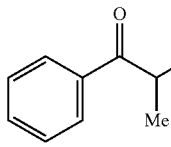 and 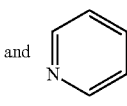 + CS$_2$ | | 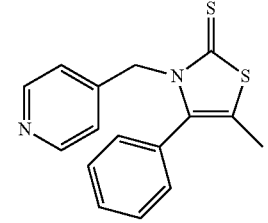 |
| Z-08 | Dehydration of reaction product of: 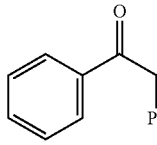 and 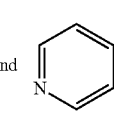 + CS$_2$ | | 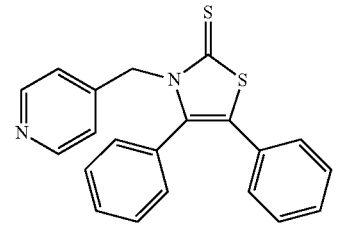 |
| Z-09 | Dehydration of reaction product of: 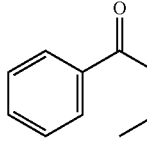 and 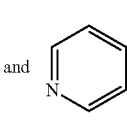 + CS$_2$ | | 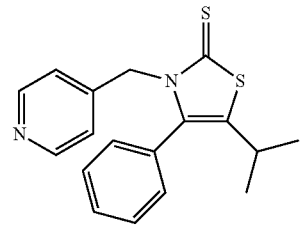 |
| Z-10 | Dehydration of reaction product of: 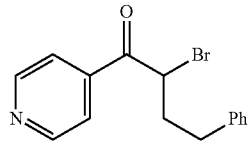 and CH$_3$NH$_2$ + CS$_2$ | | 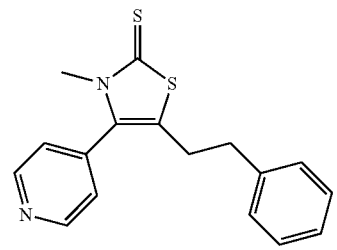 |

The compounds of General Formula (I) and General Formula (II) may be generally described as a class of compounds composed of four genera: (1) imidazole 2-thiones (in which group X is S and group Y is NH); (2) imidazole 2-ones (in which group X is O and group Y is NH); (3) thiazole 2-thiones (in which group X is S and group Y is S); and (4) thiazole 2-ones (in which group X is O and group Y is S).

According to some embodiments, in the compounds of General Formula (I) and General Formula (II), when $R^2$ is phenyl and $R^3$ is hydrogen, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; or (c) $R^1$ is Ph(CH$_2$)$_n$—, where n is 2 or 3 (i.e., group $R^1$ is 2-phenylethyl or 3-phenylpropyl); or (d) $R^1$ is a $C_1$ to $C_{10}$ heteroaliphatic group, optionally substituted with one or more aryl groups, substituted aryl groups, heteroaryl groups, substituted heteroaryl groups, or combination thereof. According to such embodiments, compounds of General Formula (I) and General Formula (II) do not include compounds in which group $R^2$ is phenyl and group $R^1$ is an unsubstituted aliphatic group other than hexyl.

In general, the provisos (a)-(d) define the scope of General Formula (I) and General Formula (II) when $R^2$ is phenyl and $R^3$ is hydrogen, based on the identity of $R^1$. For example, considering all provisos together, when $R^2$ is phenyl and $R^3$ is hydrogen, $C_1$ to $C_{10}$ aliphatic groups $R^1$ as defined under proviso (a) must be substituted with at least one substituted aryl group, at least one heteroaryl group, or at least one substituted heteroaryl group. Proviso (b) adds $R^1$=hexyl to the definition of $C_1$ to $C_{10}$ aliphatic groups from proviso (a), and proviso (c) adds 2-phenylethyl and 3-phenylpropyl to the definition of $C_1$ to $C_{10}$ aliphatic groups from proviso (a). That is, when $R^2$ is phenyl and $R^3$ is hydrogen, $C_1$ to $C_{10}$ aliphatic groups $R^1$ do not include unsubstituted aliphatic groups such as methyl, ethyl, isopropyl, or cyclohexyl but do include hexyl groups. Likewise, when $R^2$ is phenyl and $R^3$ is hydrogen, $C_1$ to $C_{10}$ aliphatic groups $R^1$ do not include aliphatic groups substituted with aryl groups that themselves are not substituted (such as phenyl), with the exception from proviso (c) that $R^1$ may be 2-phenylethyl or 3-phenylpropyl. In view of proviso (d), however, even when $R^2$ is phenyl and $R^3$ is hydrogen, $C_1$ to $C_{10}$ heteroaliphatic groups $R^1$ may be unsubstituted or substituted. When the $C_1$ to $C_{10}$ heteroaliphatic groups $R^1$ are substituted, they may be substituted with one or more aryl groups (even unsubstituted aryl groups), substituted aryl groups, heteroaryl groups, substituted heteroaryl groups, or combinations thereof.

According to some embodiments, in the compounds of General Formula (I) and General Formula (II), when $R^2$ is phenyl and $R^3$ is hydrogen, the compound having General Formula (I) or General Formula (II) is selected from the group consisting of

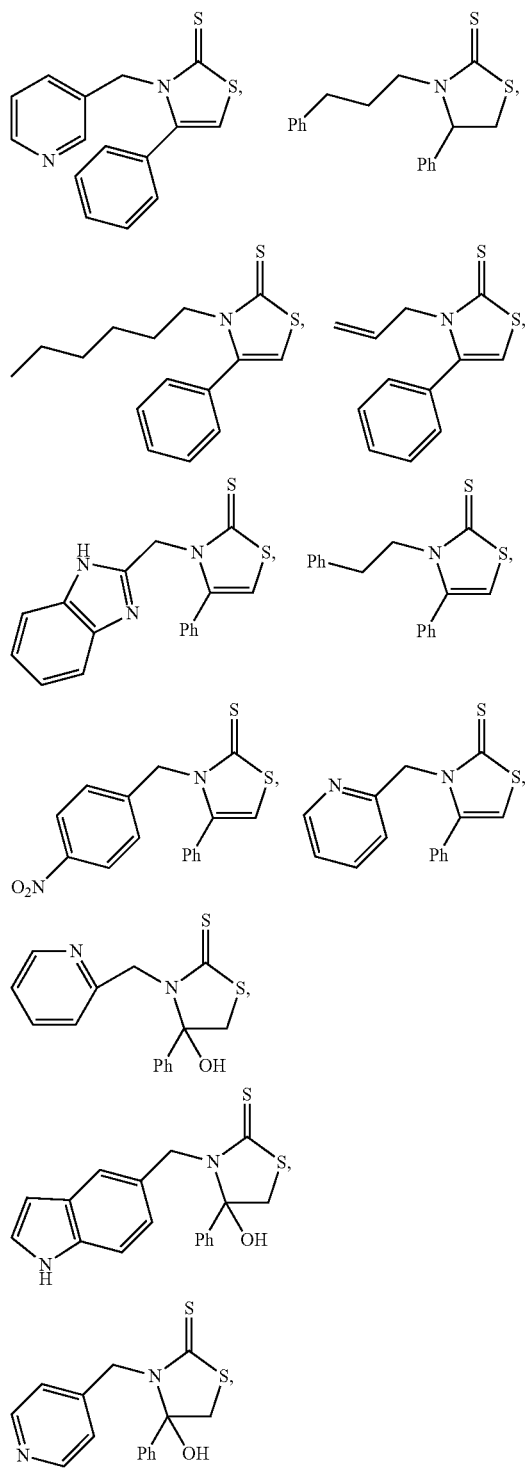

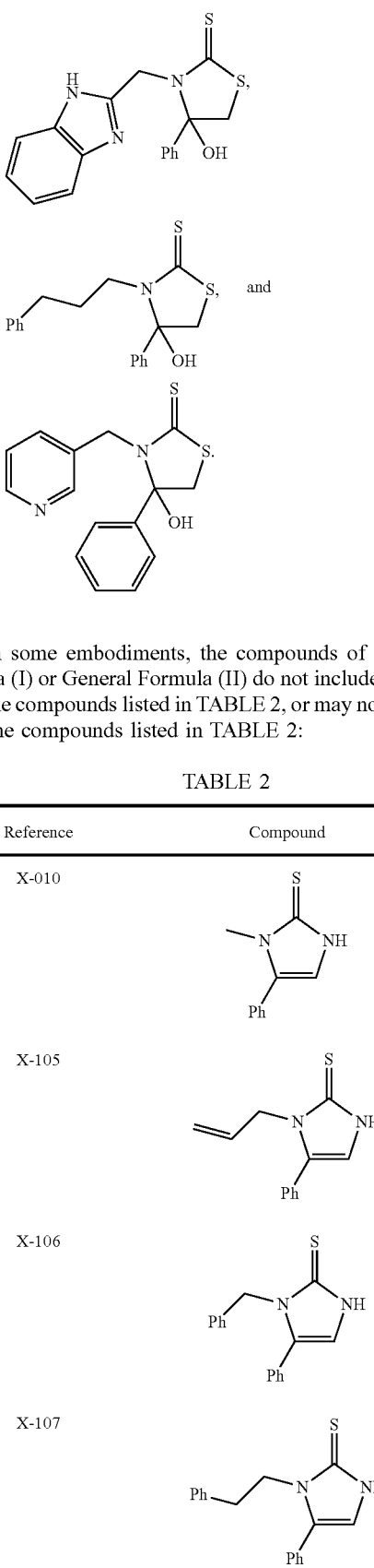

In some embodiments, the compounds of General Formula (I) or General Formula (II) do not include one or more of the compounds listed in TABLE 2, or may not include any of the compounds listed in TABLE 2:

TABLE 2

| Reference | Compound |
| --- | --- |
| X-010 | |
| X-105 | |
| X-106 | |
| X-107 | |

TABLE 2-continued

| Reference | Compound |
|---|---|
| X-108 | 1-isopropyl-5-phenyl-1H-imidazole-2(3H)-thione |
| X-109 | 1-cyclohexyl-5-phenyl-1H-imidazole-2(3H)-thione |
| X-110 | 1,5-diphenyl-1H-imidazole-2(3H)-thione |
| X-111 | 5-(4-methoxyphenyl)-1-methyl-1H-imidazole-2(3H)-thione |
| X-112 | 5-(4-chlorophenyl)-1-methyl-1H-imidazole-2(3H)-thione |
| X-113 | 1-ethyl-5-phenyl-1H-imidazol-2(3H)-one |
| X-114 | 1-butyl-5-phenyl-1H-imidazol-2(3H)-one |
| X-115 | 1-(2-morpholinoethyl)-5-phenyl-1H-imidazole-2(3H)-thione |
| X-116 | 1-methyl-5-(4-methylphenyl)-1H-imidazole-2(3H)-thione |
| X-120 | 1-hexyl-5-phenyl-1H-imidazole-2(3H)-thione |
| X-127 | 5-(3,4-dichlorophenyl)-1-methyl-1H-imidazole-2(3H)-thione |
| X-131 | 1-methyl-5-(thiophen-2-yl)-1H-imidazole-2(3H)-thione |
| X-135 | 5-(biphenyl-4-yl)-1-methyl-1H-imidazole-2(3H)-thione |
| X-136 | 3-benzyl-4-hydroxy-4-phenylthiazolidine-2-thione |
| X-137 | 3-benzyl-4-phenyl-2,3-dihydrothiazole-2-thione |

TABLE 2-continued

| Reference | Compound |
|---|---|
| X-142 | 3-propyl-4-phenyl-4-hydroxy-thiazolidine-2-thione |
| X-145 | 1-methyl-5-(3-nitrophenyl)-1H-imidazole-2(3H)-thione |
| X-149 | 1-benzyl-5-phenyl-1H-imidazol-2(3H)-one |
| X-150 | 1-propyl-5-phenyl-1H-imidazol-2(3H)-one |
| X-151 | 1-propyl-5-phenyl-1H-imidazole-2(3H)-thione |
| X-154 | 3-propyl-4-phenyl-oxazol-2(3H)-one |
| X-156 | 3-benzyl-4-phenyl-4-hydroxy-oxazolidin-2-one |
| X-157 | 3-benzyl-4-phenyl-oxazol-2(3H)-one |
| X-167 | 3-phenethyl-4-phenyl-4-hydroxy-thiazolidine-2-thione |
| X-169 | 3-(4-methoxybenzyl)-4-phenyl-4-hydroxy-thiazolidine-2-thione |
| X-179 | 3-(4-methoxybenzyl)-4-phenyl-thiazole-2(3H)-thione |
| X-181 | 3-(4-chlorobenzyl)-4-phenyl-4-hydroxy-thiazolidine-2-thione |
| X-182 | 3-(4-nitrobenzyl)-4-phenyl-4-hydroxy-thiazolidine-2-thione |
| X-184 | 3-(phenylamino)-4-phenyl-4-hydroxy-thiazolidine-2-thione |
| X-185 | N-(4-phenyl-4-hydroxy-2-thioxothiazolidin-3-yl)benzamide |
| X-194 | N-(4-phenyl-2-thioxothiazol-3(2H)-yl)benzamide |

TABLE 2-continued

| Reference | Compound |
|---|---|
| X-195 | 4-hydroxy-3-phenyl-N-phenyl-thiazolidine-2-thione (structure with Ph-N, Ph, OH, S=C-S) |
| X-211 | 3-allyl-4-hydroxy-4-phenyl-thiazolidine-2-thione |
| X-B2 | 4-(4-methoxyphenyl)-3-methyl-thiazole-2-thione |
| X-B4 | 4-(4-methoxyphenyl)-4-hydroxy-3-propyl-thiazolidine-2-thione |

Compositions and pharmaceutical compositions containing one or more compounds of General Formula (I) or General Formula (II) as described above may modify biological signaling events and, therefore, may in some embodiments be used in diagnostic or therapeutic applications. For example, various compounds having General Formula (I) or General Formula (II) may inhibit lipopolysaccharide (LPS) induction of IL-6, INF-β, and/or iNOS. LPS induction of IL-6, INF-β and iNOS occur via signaling events. IL-6, INF-β, and iNOS are themselves components of many biological signaling processes.

The activities of the compounds of General Formula (I) and (II) may be characterized by determining the concentration (i.e., the $IC_{50}$) needed to inhibit 50% of the induction. In exemplary compounds of General Formula (I) and (II), the $IC_{50}$ is in the nM range. This inhibition is not due to cell death. For example, in certain cases the concentration $TC_{50}$ of the compound required to diminish the MTS signal by 50% (MTS signal correlates with cell metabolism/viability), was over 100 times greater than the $IC_{50}$. In such examples, the mode of initiation of the signaling network may be treatment with LPS. The modification of signaling is not unique to this mode of initiation of the signaling. Compounds of General Formula (I) and (II) may also modify signaling initiated by TNF-α.

Additionally, there are several techniques that can be used to modify signaling including siRNA and genetic approaches that eliminate or enhance a particular molecule via genetic manipulation of an embryo, such as through the generation of transgenic mice. The resulting transgenic mice may be studied, or cells could be isolated from the transgenic mice and studied in culture. Both of these techniques have their drawbacks. siRNA can be problematic since siRNA itself might couple to members of the Toll family of receptors (e.g. TLR-3) which could initiate a signaling event thus confounding the interpretation of the experiment. It is well documented that transgenic mice are often altered in many ways in addition to the desired modified expression of the target gene. Regardless, compositions containing compounds of General Formula (I) or (II) may modify signaling without involving siRNA or transgenic technology. The compounds may modify multiple steps in a particular signaling pathway.

According to some embodiments, compositions containing one or more compounds of General Formula (I) and (II) may be used to probe the molecular mechanisms of normal and abnormal cellular processes. According to other embodiments, compositions containing one or more compounds of General Formula (I) and (II) may be used to probe the molecular mechanisms of normal physiology and pathology. According to other embodiments, compositions containing one or more compounds of General Formula (I) and (II) may be used as therapeutics, either alone or in combination with other drugs, for various animal and plant pathologies. According to other embodiments, compositions containing one or more compounds of General Formula (I) and (II) may be used to engender normal physiology. According to other embodiments, compositions containing one or more compounds of General Formula (I) and (II) may be used as antimicrobials. According to other embodiments, compositions containing one or more compounds of General Formula (I) and (II) may be used as aids in the processing of valuable products from biological sources. According to other embodiments, compositions containing one or more compounds of General Formula (I) and (II) may be used in diagnostic and/or prognostic assays. In non-limiting illustrative embodiments, compositions containing one or more compounds of General Formula (I) and (II) may be used to treat various pathologies such as breast cancer, sepsis, colitis, Alzheimer's Disease, horse colic, diabetes, or fatty liver disease.

Pharmaceutical compositions according to embodiments herein may include as active compounds a safe and effective amount of one or more of the compounds of General Formula (I) or (II) described above, or any pharmaceutically-acceptable salt or solvate thereof. Preferred compositions contain from about 0.01% to about 25% by weight of the active compounds, based on the total weight of the pharmaceutical composition, with most preferred compositions containing from about 0.1% to about 10% by weight of the active compounds. The pharmaceutical compositions may be administered in any way conventionally known, for example, intraperitoneally, intravenously, intramuscularly, or topically, although oral administration is preferred. Preferred compositions are in unit dosage form, i.e., pharmaceutical compositions which are available in a pre-measured form suitable for single dosage administration without requiring that the individual dosage be measured out by the user, for example, pills, tablets or ampoules.

The pharmaceutical compositions additionally may include a pharmaceutically-acceptable carrier compatible with the compounds of General Formula (I) or (II). In addition to the pharmaceutically-acceptable carrier, the pharmaceutical compositions may contain, at their art-accepted levels, additional compatible ingredients, such as additional pharmaceutical actives, excipients, formulational aids (e.g., tableting aids), colorants, flavorants, preservatives, and other materials well known to those skilled in the art.

The pharmaceutical carrier employed in conjunction with the pharmaceutical compositions according to embodiments herein is used at a concentration sufficient to provide a practical size-to-dosage relationship. Preferably, the pharmaceutical carrier comprises from about 75% to about 99.99%, preferably from about 90% to about 99.9%, by weight of the total pharmaceutical composition.

In some embodiments, the pharmaceutical compositions may include targeted or non-targeted carriers such as liposomes, particles made from biodegradable particles, polymerosomes, or ultrasound bubbles, for example. The compounds of General Formula (I) or (II) may be incorporated into the either non-targeted or targeted carriers. For the targeted particles, the targeting could be via a ligand attached to the particles, whereby the ligand is specific for a receptor overexpressed at the site of disease. Alternatively, when carriers are not present, the compounds of General Formula (I) or (II) may be conjugated to the targeting ligand directly to achieve the targeted delivery.

In some embodiments, the pharmaceutical compositions contain at least one compound having General Formula (I) or (II), or a pharmaceutically-acceptable salt or solvate thereof, in combination with at least one pharmaceutically-acceptable carrier. Exemplary pharmaceutical compositions according to some embodiments may include at least one of the compounds shown in TABLE 3 and having General Formula (I) or (II), in combination with at least one pharmaceutically-acceptable carrier:

TABLE 3

| Compound | Structure |
| --- | --- |
| COB-152 | 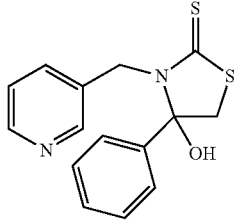 |
| COB-187 | 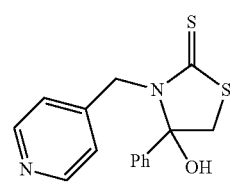 |
| COB-197 | 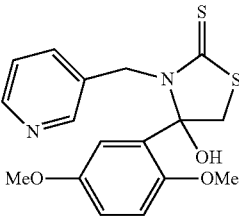 |

TABLE 3-continued

| Compound | Structure |
| --- | --- |
| COB-198 | 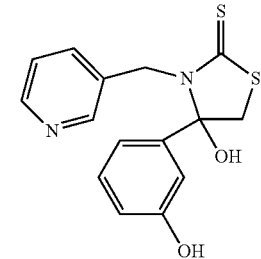 |
| COB-204 | 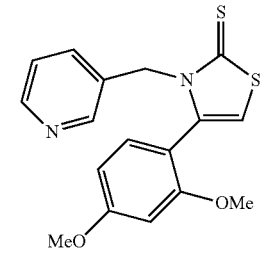 |
| COB-214 | 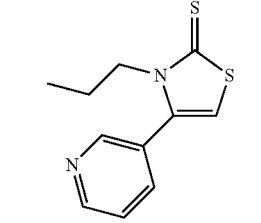 |
| COB-225 | 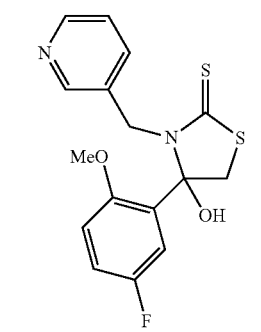 |

In some embodiments, the provided pharmaceutical compositions do not contain any of the compounds listed in TABLE 2. In some embodiments, the provided pharmaceutical compositions comprise one or more compounds listed in TABLE 2. In some embodiments, the provided pharmaceutical compositions comprise one or more compounds listed in TABLE 2 in combination with one or more compounds listed in TABLE 1. In some embodiments, the provided pharmaceutical compositions comprise one or more compounds listed in TABLE 3 in combination with one or more compounds listed in TABLE 1. In some embodiments, the provided pharmaceutical compositions comprise one or more compounds listed in TABLE 2 in combination with one or more compounds listed in TABLE 3.

EXAMPLES

The embodiments described herein will be further clarified by the following examples. The exemplary compounds synthesized and/or characterized in the Examples to follow should be understood to be illustrative in nature and in no regard limiting to the scope of the General Formulas provided.

General Synthetic Methods

Synthetic Example 1

Compounds having General Formula (I):

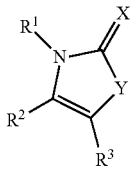

in which X=O or S; Y=NH; $R^1$, $R^2$, and $R^3$ are as described above, may be synthesized by adding an isothiocyanate or isocyanate of formula (1a):

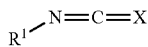

(100 mol %, X=O or S) and $Et_3N$ (50 mol. %) to an EtOH (0.01 M) solution of a hydrochloride of a methylamino ketone of formula (1b) (100 mol. %):

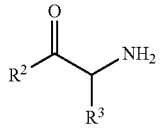

to form a reaction mixture. The reaction mixture is heated at 140° C. for 20 min using microwave irradiation. The microwave irradiation may be carried out using an Initiator Biotage Microwave Synthesizer, for example, operating at 400 W, 2.45 GHz. The solvent is then removed by means of rotary evaporation, and the product is isolated by flash chromatography. The purification is performed by eluting the crude product with 5% to 10% ethyl acetate (EtOAc) in $CH_2Cl_2$ for imidazole-2-thiones (X=S) or with EtOAc for imidazole-2-ones (X=O). Yields for this general synthetic method are typically in the range of from 15% to 65%.

Additionally, compounds having General Formula (II):

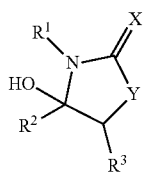

in which X=O or S; Y=NH; and $R^1$, $R^2$, and $R^3$ are as described above, may be synthesized by the above method by heating the reaction mixture at about 140° C. using means other than microwave irradiation. Without intent to be bound by theory, it is believed that microwave irradiation increases the rate of hydroxyl elimination, so as to favor formation of the compounds of General Formula (I) when the microwave irradiation is applied during heating.

Synthetic Example 2

Compounds having General Formula (II):

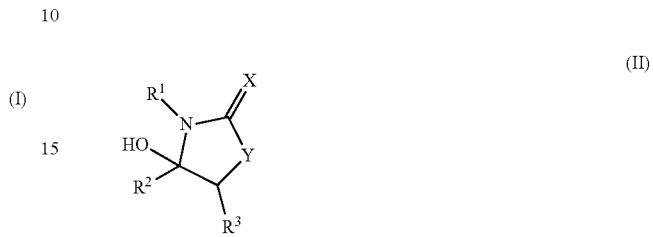

in which X=S; Y=S; and $R^1$, $R^2$, and $R^3$ are as described above may be synthesized by adding carbon disulfide ($CS_2$; 150 mol. %) and $K_2CO_3$ (50 mol. %) to a solution of an amine of the formula (2a):

(150 mol. %) in $H_2O$:EtOH (0.2 M, 1:1) and then adding a 2-bromoketone derivative of formula (2b):

(100 mol %) to form a reaction mixture. The reaction mixture is stirred in an open flask at room temperature (25° C.±2° C.) for 1 hour to 3 hours. Then, the crude reaction mixture is extracted with ethyl acetate (EtOAc; 3×10 mL), and the combined organic layers are dried over $MgSO_4$ and filtered. The solvent is evaporated by rotary evaporation. The product is isolated by flash chromatography using 10%-20% EtOAc in hexanes. In some cases, some products may precipitate during the reaction. In such cases the product may be isolated by filtration, washed thoroughly with solvent (EtOH:$H_2O$, 1:1), then dried.

Compounds having General Formula (II), in which X=O; Y=S; and $R^1$, $R^2$, and $R^3$ are as described above may be synthesized by the above method by replacing the carbon disulfide ($CS_2$) with carbonyl sulfide (C=O=S; 150 mol. %).

Synthetic Example 3

Compounds having General Formula (I), in which X=O or S; Y=S; and $R^1$, $R^2$, and $R^3$ are as described above, may be synthesized by dehydrating a compound having General Formula (II) prepared according to Synthetic Example 2 or by any other suitable method, in which groups $R^1$, $R^2$, $R^3$, X, and Y of the compound having General Formula (II) are the same as those in the desired compound having General Formula (I).

To perform the dehydration, to an ethanol solution containing 1 molar equivalent of a compound of General Formula (II), 1.2 molar equivalents of hydrochloric acid (1 M solution in ethyl acetate) are added to form a reaction mixture. The reaction mixture is submitted to microwave irradiation for 20 min at 140° C. The solvent is removed by rotary evaporation. The crude product is purified by flash chromatography.

Exemplary Compounds

Except where noted otherwise, compounds having General Formula (I) or General Formula (II) were prepared according to one of the Synthetic Examples 1-3 above. Proton NMR ($^1$H-NMR) spectra were obtained using a Brüker Avance (300 MHz) spectrometer. Carbon NMR ($^{13}$C-NMR) spectra were obtained at 75 MHz. Chemical shifts are reported in ppm on the δ scale relative to deuterated chloroform (CDCl$_3$) as an internal standard. Data are reported as follows: chemical shift, multiplicity (s=singlet, d=doublet, t=triplet, q=quartet, qt=quintet, st=sextet, m=multiplet), coupling constant in Hz, integration. HPLC analyses were performed with a Shimadzu LC-10AT machine equipped with a UV detector by employing a reverse-phase Discovery-C8 (15 cm×4.6 mm×5 μm; Supelco) column eluting with methanol (MeOH) in H$_2$O at 1 mL/min flow using the following protocol: 50% MeOH/H$_2$O, 8 min; 90% MeOH/H$_2$O, 5 min; 90% MeOH/H$_2$O, 5 min; 50% MeOH/H$_2$O, 3 min.

Example 1

COB-117

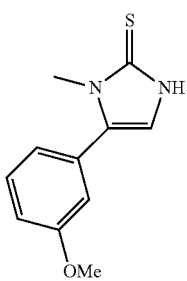

COB-117 was prepared according to Synthetic Example 1. Based on 21 mg of product recovered, the yield was 48%. For the COB-117, the following data were obtained: R$_f$ 0.4 (20% EtOAc in CH$_2$Cl$_2$); t$_R$=2.48 min; $^1$H NMR (CDCl$_3$, 300 MHz) δ 11.5 (s, 1H, NH), 7.40-7.34 (m, 1H, Ph), 6.99-6.91 (m, 2H, Ph), 6.87 (s, 1H, Ph), 6.75 (s, 1H, $^4$CH), 3.84 (s, 3H, OCH$_3$), 3.60 (s, 3H, NCH$_3$); $^{13}$C NMR (CDCl$_3$, 75 MHz) δ 161.7, 160.1, 132.7, 130.3, 129.9, 121.3, 114.8, 114.6, 112.1, 55.6, 32.9.

Example 2

COB-118

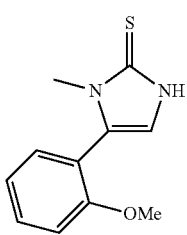

COB-118 was prepared according to Synthetic Example 1. Based on 14.8 mg of product recovered, the yield was 34%. For the COB-118, the following data were obtained: R$_f$ 0.24 (10% EtOAc in CH$_2$Cl$_2$); t$_R$=2.46 min; $^1$H NMR (CDCl$_3$, 300 MHz) δ 10.8 (s, 1H, NH), 7.47-6.97 (m, 4H, Ph), 6.68 (d, J=2 Hz, 1H, CH), 3.82 (s, 3H, OCH$_3$), 3.42 (s, 3H, OCH$_3$); $^{13}$C NMR (CDCl$_3$, 75 MHz) δ 158.0, 132.2, 131.6, 121.0, 117.5, 112.4, 111.2, 55.6, 32.6.

Example 3

COB-119

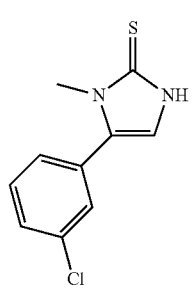

COB-119 was prepared according to Synthetic Example 1. Based on 12 mg of product recovered, the yield was 28%. For the COB-119, the following data were obtained: 12 mg (28%); R$_f$ 0.25 (10% EtOAc in CH$_2$Cl$_2$); t$_R$=2.69 min; $^1$H NMR (CDCl$_3$, 300 MHz) δ 11.11 (s, 1H, NH), 7.42-7.22 (m, 4H, Ph), 6.76 (s, 1H, CH), 3.60 (s, 3H, CH$_3$); $^{13}$C NMR (CDCl$_3$, 75 MHz) δ 162.8, 135.3, 131.5, 130.6, 130.3, 129.6, 129.0, 127.1, 112.4, 33.0.

Example 4

COB-123

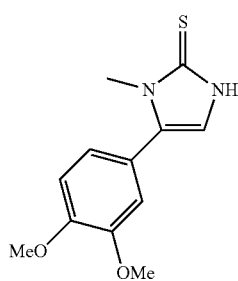

COB-123 was prepared according to Synthetic Example 1. Based on 29.8 mg of product recovered, the yield was 60%. For the COB-123, the following data were obtained: R$_f$ 0.27 (10% EtOAc in CH$_2$Cl$_2$); t$_R$=3.62 min; $^1$H NMR (CDCl$_3$, 300 MHz) δ 11.74 (s, 1H, NH), 7.28-6.82 (m, 3H, Ph), 6.73 (s, 1H, CH), 3.91 (s, 6H, CH$_3$), 3.57 (s, 3H, CH$_3$); $^{13}$C NMR (CDCl$_3$, 75 MHz) δ 160.9, 150.1, 149.4, 132.6, 122.0, 121.1, 112.4, 111.8, 111.6, 56.2, 32.7.

Example 5

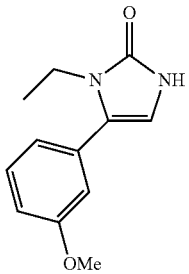

COB-124

COB-124 was prepared according to Synthetic Example 1. Based on 10 mg of product recovered, the yield was 25%. For the COB-124, the following data were obtained: $R_f$ 0.27 (EtOAc); $t_R$=7.15 min; $^1$H NMR (CDCl$_3$, 300 MHz) δ 9.8 (s, 1H, NH), 7.33 (t, 1H, Ph), 6.95-6.88 (m, 3H, Ph), 6.31 (s, 1H, CH), 3.83 (s, 3H, CH$_3$), 3.80 (t, J=7.71 Hz, 2H, CH$_2$), 1.17 (q, J=7.71 Hz, 3H, CH$_3$); $^{13}$C NMR (CDCl$_3$, 75 MHz) δ 160.1, 155.2, 131.5, 130.1, 125.7, 120.8, 114.2, 113.8, 106.0, 55.6, 36.8, 15.0.

Example 6

COB-125

COB-125 was prepared according to Synthetic Example 1. Based on 15 mg of product recovered, the yield was 37%. For the COB-125, the following data were obtained: $R_f$ 0.27 (EtOAc); $t_R$=3.19 min $^1$H NMR (CDCl$_3$, 300 MHz δ 10.69 (s, 1H, NH), 7.36-7.22 (m, 4H, Ph), 6.35 (s, 1H, CH), 3.80 (t, J=7.71 Hz, 2H, CH$_2$), 1.18 (q, J=7.71 Hz, 3H, CH$_3$); $^{13}$C NMR (CDCl$_3$, 75 MHz) δ 155.5, 135.0, 132.0, 130.3, 128.5, 128.3, 126.4, 124.3, 107.1, 36.8, 15.0.

Example 7

COB-126

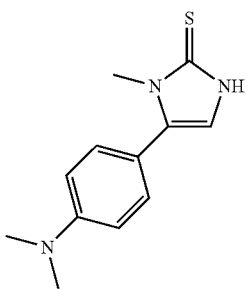

COB-126 was prepared according to Synthetic Example 1. Based on 17.3 mg of product recovered, the yield was 37%. For the COB-126, the following data were obtained: $R_f$ 0.33 (20% EtOAc in CH$_2$Cl$_2$); $t_R$=6.69 min; $^1$H NMR (CDCl$_3$, 300 MHz) δ 10.48 (s, 1H, NH), 7.18 (d, J=7 Hz, 2H, Ph), 6.75 (d, J=8.8 Hz, 2H, Ph), 6.62 (s, 1H, CH), 3.55 (s, 3H, CH$_3$), 3.01 (s, 6H, NCH$_3$); $^{13}$C NMR (CDCl$_3$, 75 MHz) δ 161.4, 151.0, 133.5, 130.2, 115.9, 112.4, 110.7, 40.5, 32.7.

Example 8

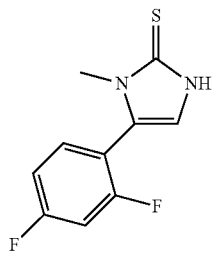

COB-128

COB-128 was prepared according to Synthetic Example 1. Based on 10.4 mg of product recovered, the yield was 23%. For the COB-128, the following data were obtained: $R_f$ 0.37 (20% EtOAc in CH$_2$Cl$_2$); $t_R$=2.45 min; $^1$H NMR (CDCl$_3$, 300 MHz) δ 11.4 (s, 1H, NH), 7.30-7.26 (m, 1H, Ph), 7.01-6.93 (m, 2H, Ph), 6.78 (s, 1H, $^4$CH), 3.49 (s, 3H, NCH$_3$).

Example 9

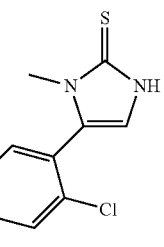

COB-129

COB-129 was prepared according to Synthetic Example 1. Based on 11.9 mg of product recovered, the yield was 23%. For the COB-129, the following data were obtained: $R_f$ 0.4 (20% EtOAc in CH$_2$Cl$_2$); $t_R$=3.21 min; $^1$H NMR (CDCl$_3$, 300 MHz) δ 11.02 (s, 1H, NH), 7.55 (d, J=2 Hz, 1H, Ph), 7.37-7.34 (m, 2H, Ph), 6.75 (s, 1H, CH), 3.42 (s, 3H, NCH$_3$); $^{13}$C NMR (CDCl$_3$, 75 MHz) δ 162.3, 137.1, 136.4, 133.6, 130.5, 130.4, 127.9, 109.2, 32.5.

Example 10

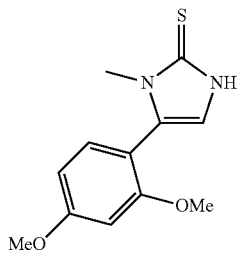

COB-130

COB-130 was prepared according to Synthetic Example 1. Based on 10 mg of product recovered, the yield was 20%. For the COB-130, the following data were obtained: $R_f$ 0.31 (20% EtOAc in $CH_2Cl_2$); $t_R$=5.33 min; $^1$H NMR ($CDCl_3$, 300 MHz) δ 10.99 (s, 1H, NH), 7.11-7.08 (m, 1H, Ph), 6.62 (s, 1H, CH), 6.54-6.51 (in, 2H, Ph), 3.85 (s, 3H, $OCH_3$), 3.78 (s, 3H, $OCH_3$), 3.39 (s, 3H, $NCH_3$); $^{13}$C NMR ($CDCl_3$, 75 MHz) δ 162.6, 160.8, 159.2, 132.9, 129.7, 112.2, 110.1, 104.9, 99.0, 55.8, 55.6, 32.4.

Example 11

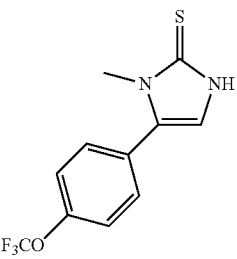 [SMILES: Cn1c(-c2ccc(OC(F)(F)F)cc2)c[nH]c1=S]

COB-132

COB-132 was prepared according to Synthetic Example 1. Based on 20 mg of product recovered, the yield was 40%. For the COB-132, the following data were obtained: $R_f$ 0.4 (20% EtOAc in $CH_2Cl_2$); $t_R$=2.43 min; $^1$H NMR ($CDCl_3$, 300 MHz) δ 11.59 (s, 1H, NH), 6.99-6.89 (in, 2H, Ph), 6.77 (d, J=3 Hz, 1H, Ph), 6.71 (s, 1H, CH), 3.78 (s, 3H, $OCH_3$), 3.76 (s, 3H, $OCH_3$), 3.44 (s, 3H, $NCH_3$); $^{13}$C NMR ($CDCl_3$, 75 MHz) δ 160.7, 153.7, 152.1, 129.7, 118.1, 117.9, 116.0, 112.6, 112.2, 56.1, 56.05, 32.6.

Example 12

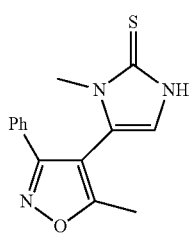

COB-133

COB-133 was prepared according to Synthetic Example 1. Based on 18.5 mg of product recovered, the yield was 34%. For the COB-133, the following data were obtained: $R_f$ 0.4 (20% EtOAc in $CH_2Cl_2$); $t_R$=2.45 min; $^1$H NMR ($CDCl_3$, 300 MHz) δ 11.94 (s, 1H, NH), 7.52-7.36 (m, 5H, Ph), 6.84 (s, 1H, CH), 3.15 (s, 3H, $NCH_3$), 2.42 (s, 3H, $CH_3$); $^{13}$C NMR ($CDCl_3$, 75 MHz) δ 171.0, 161.2, 130.9, 130.6, 129.7, 129.4, 128.3, 128.0, 127.3, 121.1, 103.4, 32.0, 11.7.

Example 13

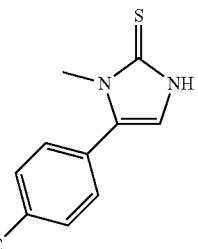

COB-134

COB-134 was prepared according to Synthetic Example 1. Based on 10.3 mg of product recovered, the yield was 19%. For the COB-134, the following data were obtained: $R_f$ 0.4 (20% EtOAc in $CH_2Cl_2$); $t_R$=3.03 min; $^1$H NMR ($CDCl_3$, 300 MHz) δ 11.22 (s, 1H, NH), 7.41-7.30 (m, 4H, Ph), 6.76 (s, 1H, CH), 3.59 (s, 3H, $CH_3$); $^{13}$C NMR ($CDCl_3$, 75 MHz) δ 149.72, 131.21, 130.4, 127.1, 122.1, 121.5, 118.7, 112.3, 32.7.

Example 14

COB-138

COB-138 was prepared according to Synthetic Example 1. Based on 16 mg of product recovered, the yield was 37%. For the COB-138, the following data were obtained: $R_f$ 0.32 (20% EtOAc in $CH_2Cl_2$); $t_R$=3.22 min; $^1$H NMR ($CDCl_3$, 300 MHz) δ 11.19 (s, 1H, NH), 7.77 (d, J=8.5 Hz, 2H, Ph), 7.49 (d, J=8.5 Hz, 2H, Ph), 6.86 (s, 1H, CH), 3.64 (s, 3H, $CH_3$); $^{13}$C NMR ($CDCl_3$, 75 MHz) δ 163.5, 133.1, 133.0, 131.1, 129.1, 118.3, 113.3, 113.0, 33.2.

Example 15

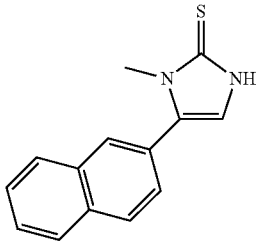 [SMILES: Cn1c(-c2ccc3ccccc3c2)c[nH]c1=S]

COB-139

COB-139 was prepared according to Synthetic Example 1. Based on 20 mg of product recovered, the yield was 41%. For the COB-139, the following data were obtained: $R_f$ 0.39 (20% EtOAc in $CH_2Cl_2$); $t_R$=2.76 min; $^1$H NMR (CDCl$_3$, 300 MHz) δ 11.50 (s, 1H, NH), 7.94-7.84 (m, 4H, Ar), 7.58-7.53 (m, 2H, Ar), 7.45-7.41 (m, 1H, Ar), 6.86 (s, 1H, CH), 3.67 (s, 3H, CH$_3$); $^{13}$C NMR (CDCl$_3$, 75 MHz) δ 161.9, 133.4, 133.36, 132.9, 129.1, 128.4, 128.36, 128.1, 127.3, 127.2, 126.2, 125.9, 112.3, 33.1.

Example 16

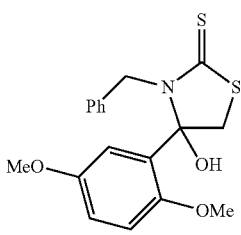 [SMILES: COc1ccc(OC)c(C2(O)CSC(=S)N2Cc2ccccc2)c1]

COB-143

COB-143 was prepared according to Synthetic Example 2. Based on 65 mg of product recovered, the yield was 93%. For the COB-143, the following data were obtained: $R_f$ 0.1 (1.0% EtOAc in hexanes); $t_R$=14.45 min; $^1$H NMR (DMSO-d$_6$, 300 MHz) δ 7.76 (s, 1H, OH), 7.24 (d, J=3.1 Hz, 1H, Ar), 7.07-6.99 (m, 5H, Ph), 6.79 (dd, J=3.1, 8.9 Hz, 1H, Ar), 6.53 (d, J=3.1 Hz, 1H, Ar), 4.84 (d, J=15 Hz, 1H, PhCHH), 4.38 (d, J=15 Hz, 1H, PhCHH), 3.86 (d, J=12 Hz, 1H, SCHH), 3.72 (s, 3H, OCH$_3$), 3.40 (s, 3H, OCH$_3$), 3.28 (d, J=12 Hz, 1H, SCHH); $^{13}$C NMR (DMSO-d$_6$, 75 MHz) δ 196.0, 152.5, 150.3, 136.7, 128.4, 128.0, 127.2, 126.3, 114.9, 113.3, 112.0, 97.5, 55.5, 55.3, 48.1.

Example 17

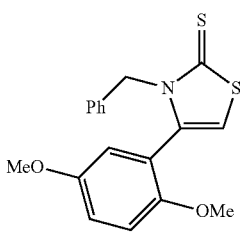 [SMILES: COc1ccc(OC)c(-c2csc(=S)n2Cc2ccccc2)c1]

COB-144

COB-144 was prepared from COB-143 according to Synthetic Example 3. Based on 56.4 mg of product recovered, the yield was 94%. For the COB-144, the following data were obtained: $R_f$ 0.17 (10% EtOAc in hexanes); $t_R$=14.47 min; $^1$H NMR (CDCl$_3$, 300 MHz) δ 7.15-7.13 (m, 3H, Ar), 6.96-6.82 (m, 4H, Ar), 6.42 (s, 1H, CH), 6.34 (d, J=3 Hz, 1H, Ar), 5.32 (s, 2H, CH$_2$), 3.63 (s, 3H, OCH$_3$), 3.57 (s, 3H, OCH$_3$); $^{13}$C NMR (CDCl$_3$, 75 MHz) δ 187.3, 152.6, 151.0, 140.8, 135.5, 128.1, 127.1, 126.7, 119.2, 117.1, 117.0, 112.5, 110.3, 55.7, 55.5, 50.0.

Example 18

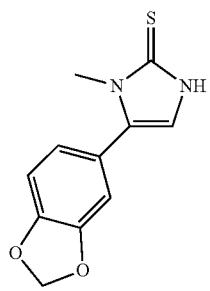 [SMILES: Cn1c(-c2ccc3c(c2)OCO3)c[nH]c1=S]

COB-146

COB-146 was prepared according to Synthetic Example 1. Based on 16.4 mg of product recovered, the yield was 35%. For the COB-146, the following data were obtained: $R_f$ 0.37 (20% EtOAc in CH$_2$Cl2); $t_R$=2.29 min.

Example 19

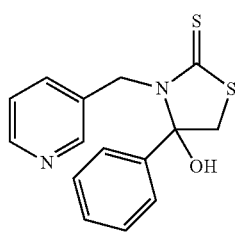

COB-152

COB-152 was prepared according to Synthetic Example 2. Based on 33.8 mg of product recovered, the yield was 89%. For the COB-152, the following data were obtained: 33.8 mg (89%); $R_f$ 0.4 (60% EtOAc in hexanes); $t_R$=11.78 min; $^1$H NMR (DMSO-d$_6$, 300 MHz) δ 8.36-8.35 (m, 2H, Py), 7.86 (s, 1H, OH), 7.59 (dt, J=7.9 Hz, 1H, Py), 7.39-7.34 (m, 5H, Ph), 4.80 (d, J=15 Hz, 1H, PyCHH), 4.52 (d, J=15 Hz, 1H, PyCHH), 3.74 (d, J=12 Hz, 1H, SCHH), 3.68 (d, J=12 Hz, 1H, SCHH); $^{13}$C NMR (DMSO-d$_6$, 75 MHz) δ 195.8, 149.0, 147.8, 140.5, 135.3, 132.3, 128.9, 128.5, 125.6, 122.9, 100.2, 46.4, 42.4.

Example 20

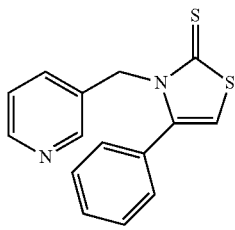

COB-153

COB-153 was prepared from COB-152 according to Synthetic Example 3. Based on 23.4 mg of product recovered, the yield was 90%. For the COB-153, the following data were obtained: Was prepared from COB-152 following the general procedure to afford 23.4 mg (90%). $R_f$ 0.46 (60% EtOAc in hexanes); $t_R$=9.25 min; $^1$H NMR (CDCl$_3$, 300 MHz) δ 8.38 (dd, J=1.5, 4.8 Hz, 1H, Py), 7.94 (d, J=1.6 Hz, 1H, Py), 7.43-7.29 (m, 4H, Ph), 7.10-7.03 (m, 3H, Ph, Py), 6.43 (s, 1H, CH), 5.36 (s, 2H, PyCH$_2$); $^{13}$C NMR (CDCl$_3$, 75 MHz) δ 189.4, 149.2, 148.9, 144.5, 135.5, 131.4, 130.5, 130.45, 129.6, 129.2, 123.6, 109.3, 48.5.

Example 21

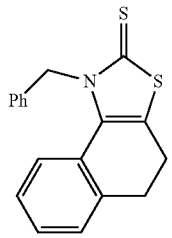 [SMILES: S=c1sc2c(n1Cc1ccccc1)-c1ccccc1CC2]

COB-161

COB-161 was prepared by performing the synthetic method according to Synthetic Example 2 using benzylamine as the compound of formula (2a) and 2-bromo-3,4-dihydro-1(2H)-naphthalenone (2-bromo-1-tetralone) as the compound of formula (2b) and proceeding to dehydrate an impure 4-hydroxy-thiazolidine-2-thione intermediate, without isolation of the intermediate, by performing the method of Synthetic Example 3. Based on 47.5 mg of product recovered, the overall yield after the two-step synthesis was 66%. For the COB-161, the following data were obtained: $R_f$ 0.4 (20% EtOAc in hexanes); $t_R$=16.55 min; $^1$H NMR (CDCl$_3$, 300 MHz) δ 7.43-7.07 (m, 9H, Ph), 5.76 (s, 2H, PhCH$_2$), 2.96 (t, J=6.9 Hz, 2H, CH$_2$), 2.72 (t, J=7.9 Hz, 2H, CH$_2$); $^{13}$C NMR (CDCl$_3$, 75 MHz) δ 188.3, 138.5, 136.6, 135.4, 129.2, 129.0, 128.3, 127.7, 127.4, 127.0, 126.2, 123.8, 122.3, 53.1, 29.9, 22.8.

Example 22

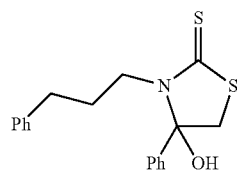 [SMILES: OC1(c2ccccc2)CSC(=S)N1CCCc1ccccc1]

COB-168

COB-168 was prepared according to Synthetic Example 2 on a 1.89-mmol scale. Based on 365 mg of product recovered, the yield was 88%. For the COB-168, the following data were obtained: Compound COB-168 was prepared affording 365 mg (88%); $R_f$ 0.42 (10% EtOAc in toluene); $t_R$=17.15 min; $^1$H NMR (DMSO-d$_6$, 300 MHz) δ 7.72 (s, 1H, OH), 7.43-7.39 (m, 5H, Ar), 7.24-7.19 (m, 2H, Ar), 7.16-7.13 (m, 1H, Ar), 7.03-7.01 (m, 2H, Ar), 3.60-3.52 (m, 3H, SCH$_2$ and NCHH), 3.19 (m, 1H, NCHH), 2.49-2.39 (m, 2H, CH$_2$), 1.89-1.81 (m, 1H, PhCHH), 1.69-1.61 (m, 1H, PhCHH); $^{13}$C NMR (DMSO-d$_6$, 75 MHz) δ 193.9, 141.2, 140.9, 128.8, 128.6, 128.2, 127.9, 125.7, 125.3, 100.0, 45.7, 42.6, 32.5, 28.6.

Example 23

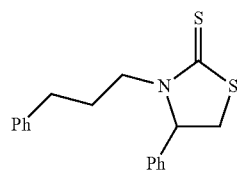

COB-178

COB-178 may be prepared from COB-168 according to Synthetic Example 3.

Example 24

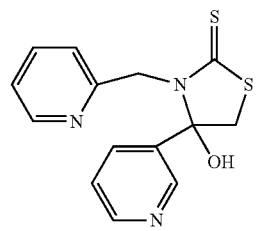

COB-176

COB-176 was prepared according to Synthetic Example 2 on a 1.5-mmol scale. Based on 104 mg of product recovered, the yield was 23%. For the COB-176, the following data were obtained: $R_f$ 0.23 (10% MeOH in EtOAc); $t_R$=2.76 min; $^1$H NMR (CDCl$_3$, 300 MHz) δ 8.75 (d, J=2 Hz, 1H, Ar), 8.53 (dd, J=1.5, 5 Hz, 1H, Ar), 8.28 (d, J=1.5 Hz, 1H, Ar), 8.00 (dd, J=1.3, 4.8 Hz, 1H, Ar), 7.77-7.20 (m, 2H, Ar), 7.28 (dd, J=4.8, 7.9 Hz, 1H, Ar), 7.19 (s, 1H), 7.03 (dd, J=4.9, 7.8 Hz, 1H, Ar), 5.7 (d, J=14.9 Hz, 1H, NCHH), 4.26 (d, J=14.9 Hz, 1H, NCHH), 3.74 (d, J=12.2 Hz, 1H, SCHH), 3.54 (d, J=12.2 Hz, 1H, SCHH); $^{13}$C NMR (CDCl$_3$, 75 MHz) δ 196.9, 150.4, 149.0, 147.6, 147.3, 138.3, 136.7, 134.0, 133.6, 123.9, 123.8, 100.0, 47.0, 43.5.

Example 25

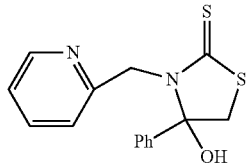

COB-180

COB-180 was prepared according to Synthetic Example 2 on a 1.88-mmol scale. Based on 300 mg of product recovered, the yield was 84%. For the COB-180, the following data were obtained: R$_f$ 0.34 (20% EtOAc in hexanes); t$_R$=10.8 min; $^1$H NMR (DMSO-d$_6$, 300 MHz) δ 8.42 (d, J=4.8 Hz, 1H, Ar), 8.27 (s, 1H, OH), 7.75-7.70 (m, 1H, Ar), 7.51-7.48 (m, 2H, Ar), 7.42-7.21 (m, 5H, Ar), 4.95 (d, J=16.2 Hz, 1H, NCHH), 4.38 (d, J=16.2 Hz, 1H, NCHH), 3.79 (d, J=12.1 Hz, 1H, SCHH), 3.71 (d, J=12.1 Hz, 1H, SCHH); $^{13}$C NMR (DMSO-d$_6$, 75 MHz) δ 196.6, 155.2, 148.1, 140.8, 136.7, 128.8, 128.6, 125.8, 122.2, 122.1, 99.8, 50.7, 43.1.

Example 26

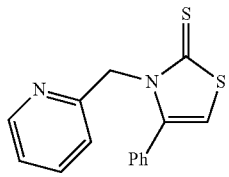 [SMILES: S=c1scc(-c2ccccc2)n1Cc1ccccn1]

COB-189

COB-189 was prepared from COB-180 according to Synthetic Example 3 on a 0.5-mmol scale. Based on 129.4 mg of product recovered, the yield was 91%. For the COB-189, the following data were obtained: R$_f$ 0.16 (20% EtOAc in hexanes); t$_R$=6.05 min; $^1$H NMR (CDCl$_3$, 300 MHz) δ 8.460-8.39 (m, 1H, Ar), 7.56-7.50 (m, 1H, Ar), 7.35-6.98 (m, 7H, Ar), 6.47 (s, 1H, CH), 5.37 (s, 2H, NCH$_2$); $^{13}$C NMR (CDCl$_3$, 75 MHz) δ 189.2, 155.0, 149.7, 145.4, 136.7, 130.8, 130.1, 129.6, 129.0, 122.5, 121.7, 52.8.

Example 27

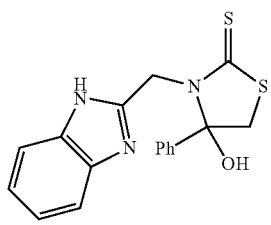

COB-183

COB-183 was prepared according to Synthetic Example 2 on a 1.88-mmol scale. Based on 214 mg of product recovered, the yield was 50%. For the COB-183, the following data were obtained: R$_f$ 0.16 (20% EtOAc in hexanes); t$_R$=12.28 min; $^1$H NMR (DMSO-d$_6$, 300 MHz) δ 12.39 (s, 1H, NH), 8.76 (s, 1H, OH), 7.61-7.37 (m, 7H, Ar), 7.18-7.16 (m, 2H, Ar), 5.18 (d, J=16.5 Hz, 1H, NCHH), 4.40 (d, J=16.5 Hz, 1H, NCHH), 3.80 (d, J=12 Hz, 1H, SCHH), 3.70 (d, J=12 Hz, 1H, SCHH); $^{13}$C NMR (DMSO-d$_6$, 75 MHz) δ 198.2, 150.0, 140.5, 129.0, 128.6, 126.1, 121.9, 99.7, 43.9, 43.5.

Example 28

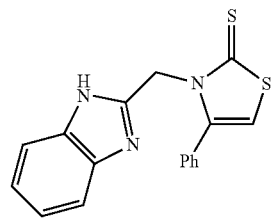 [SMILES: S=c1scc(-c2ccccc2)n1Cc1nc2ccccc2[nH]1]

COB-192

COB-192 was prepared from COB-183 according to Synthetic Example 3 on a 0.07-mmol scale. Based on 13 mg of product recovered, the yield was 63%. For the COB-192, the following data were obtained: R$_f$ 0.4 (5% EtOAc in toluene); t=6.95 min; $^1$H NMR (DMSO-d$_6$, 300 MHz) δ 12.4 (s, 1H, NH), 7.58-7.55 (m, 3H, Ar), 7.45-7.38 (m, 4H, Ar), 7.16-7.11 (m, 3H, Ar and SCH), 5.41 (s, 2H, NCH$_2$); $^{13}$C NMR (DMSO-d$_6$, 75 MHz) δ 188.0, 148.9, 144.5, 142.9, 134.1, 130.4, 129.8, 129.2, 128.7, 122.1, 121.2, 118.6, 111.2, 109.6, 45.7.

Example 29

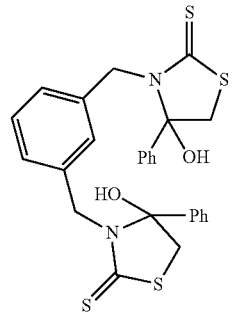 [SMILES: OC1(c2ccccc2)CSC(=S)N1Cc1cccc(CN2C(=S)SCC2(O)c2ccccc2)c1]

COB-186

COB-186 was prepared according to Synthetic Example 2 on a 1.88-mmol scale. Based on 640 mg of product recovered, the yield was 65%. For the COB-186, the following data were obtained: R$_f$ 0.16 (20% EtOAc in hexanes); t$_R$=17.17 min; $^1$H NMR (DMSO-d$_6$, 300 MHz) δ 7.74-7.72 (m, 2H, OH), 7.34-7.16 (m, 10H, Ar), 6.99-6.91 (m, 4H, Ar), 4.75-4.64 (m, 2H, NCHH), 4.47-4.38 (m, 2H, NCHH), 3.72 (d, J=12.1 Hz, 2H, SCHH), 3.60 (d, J=12.1 Hz, 2H, SCHH); $^{13}$C NMR (DMSO-d$_6$, 75 MHz) δ 195.5, 140.59, 140.55, 136.08, 136.02, 128.9, 128.7, 128.4, 128.2, 127.2, 126.8, 126.6, 125.7, 125.6, 100.3, 100.26, 48.6, 42.4.

Example 30

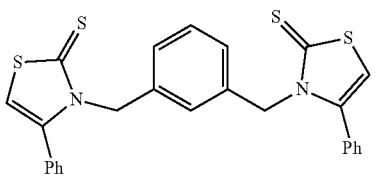

COB-193

COB-193 was prepared from COB-186 according to Synthetic Example 3 on a 0.25-mmol scale. Based on 110 mg of product recovered, the yield was 90%. For the COB-193, the following data were obtained: $R_f$ 0.37 (20% EtOAc in hexanes); $t_R$=17.14 min; $^1$NMR (CDCl$_3$, 300 MHz) δ 7.33-7.16 (m, 6H, Ar), 7.03-6.93 (m, 5H, Ar), 6.67 (d, 2H, Ar), 6.41 (s, 2H, CH), 6.27 (s, 1H, Ar), 5.2 (s, 4H, NCH$_2$); $^{13}$C NMR (CDCl$_3$, 75 MHz) δ 189.1, 145.1, 135.9, 130.6, 130.1, 129.7, 128.9, 128.8, 126.2, 124.8, 109.1, 50.8.

Example 31

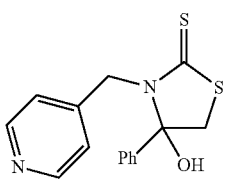

COB-187

COB-187 was prepared according to Synthetic Example 2 on a 1.88-mmol scale. Based on 70 mg of product recovered, the yield was 20%. For the COB-187, the following data were obtained: $R_f$ 0.3 (10% EtOAc in toluene); $t_R$=8.59 min; $^1$H NMR (DMSO-d$_6$, 300 MHz) δ 8.39-8.37 (d, 2H, Ar), 7.84 (s, 1H, OH), 7.39-7.35 (m, 5H, Ar), 7.16-7.15 (m, 2H, Ar), 4.80 (d, J=16.1 Hz, 1H, NCHH), 4.51 (d, J=16.1 Hz, 1H, NCHH), 3.78 (d, J=12.1 Hz, 1H, SCHH), 3.71 (d, J=12.1 Hz, 1H, SCHH); $^{13}$C NMR (DMSO-d$_6$, 75 MHz) δ 196.0, 148.9, 145.6, 140.5, 128.9, 128.5, 125.6, 122.3, 100.1, 47.8, 42.4.

Example 32

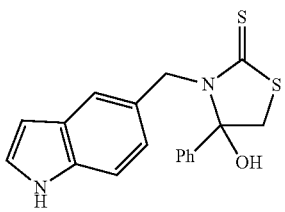 [SMILES: OC1(c2ccccc2)CSC(=S)N1Cc1ccc2[nH]ccc2c1]

COB-188

COB-188 was prepared according to Synthetic Example 2 on a 1.88-mmol scale. Based on 107 mg of product recovered, the yield was 25%. For the COB-188, the following data were obtained: $R_f$ 0.25 (10% EtOAc in toluene); $t_R$=14.41 min; $^1$H NMR (CDCl$_3$, 300 MHz) δ 8.91 (s, 1H, NH), 7.45-7.35 (m, 5H, Ph), 7.31-7.14 (m, 5H, Ar), 6.47 (s, 1H, OH), 5.82 (d, J=14.5 Hz, 1H, NCHH), 4.21 (d, J=14.5 Hz, 1H, NCHH), 3.61 (d, J=12.1 Hz, 1H, SCHH), 3.38 (d, J=12.1 Hz, 1H, SCHH); $^{13}$C NMR (CDCl$_3$, 75 MHz) δ 198.4, 139.6, 135.4, 129.3, 128.9, 127.9, 127.8, 126.2, 124.9, 122.8, 121.2, 111.5, 102.9, 100.8, 49.6, 44.0.

Example 33

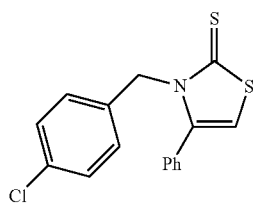 [SMILES: S=c1scc(-c2ccccc2)n1Cc1ccc(Cl)cc1]

COB-190

COB-190 was prepared according to Synthetic Example 3 on a 0.2-mmol scale. Based on 44 mg of product recovered, the yield was 69%. For the COB-190, the following data were obtained: $R_f$ 0.5 (20% EtOAc in hexanes); $t_R$=17.12 min.

Example 34

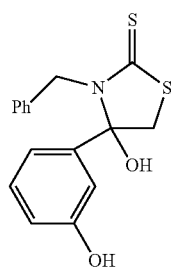 [SMILES: Oc1cccc(C2(O)CSC(=S)N2Cc2ccccc2)c1]

COB-196

COB-196 was prepared according to Synthetic Example 2 on a 1.5-mmol scale. Based on 63.4 mg of product recovered, the yield was 20%. For the COB-196, the following data were obtained: $R_f$ 0.24 (10% EtOAc in toluene); $t_R$=12.87 min; $^1$H NMR (DMSO-d$_6$, 300 MHz) δ 9.56 (s, 1H, ArOH), 7.67 (s, 1H, OH), 7.23-7.13 (m, 6H, Ar), 6.83-6.71 (m, 3H, Ar), 4.89 (d, J=15.3 Hz, 1H, NCHH), 4.38 (d, J=15.3 Hz, 1H, NCHH), 3.73 (d, J=12 Hz, 1H, SCHH), 3.56 (d, J=12 Hz, 1H, SCHH); $^{13}$C NMR (DMSO-d$_6$, 75 MHz) δ 195.1, 157.5, 142.5, 136.7, 127.7, 127.6, 100.5, 40.3.

Example 35

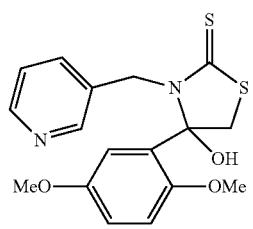

COB-197

COB-197 was prepared according to Synthetic Example 2 on a 3-mmol scale. Based on 450 mg of product recovered, the yield was 62%. For the COB-197, the following data were obtained: $R_f$ 0.4 (60% EtOAc in hexanes); $t_R$=5.33 min; $^1$H NMR (DMSO-d$_6$, 300 MHz) δ 8.27-8.25 (m, 1H, Ar), 8.09 (d, 1H, Ar), 7.87 (s, 1H, OH), 7.42 (d, 1H, Ar), 7.25 (d, 1H, Ar), 7.11-7.07 (m, 1H, Ar), 6.80-6.77 (m, 1H, Ar), 6.50 (d, 1H, Ar), 4.91 (d, J=15.3 Hz, 1H, NCHH), 4.38 (d, J=15.3 Hz, 1H, NCHH), 3.85 (d, J=12 Hz, 1H, SCHH), 3.72 (s, 3F1, OCH$_3$), the signal corresponding to the second MeO overlaps with the water peak, 3.28 (d, J=12 Hz, 1H, SCHH); $^{13}$C NMR (DMSO-d$_6$, 75 MHz) δ 194.4, 150.7, 148.1, 147.1, 145.6, 133.5, 130.3, 126.3, 120.5, 113.2, 111.3, 109.9, 95.4, 53.6, 53.4 43.8.

Example 36

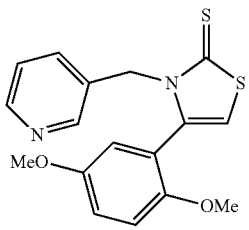 [SMILES: COc1ccc(OC)c(-c2csc(=S)n2Cc2cccnc2)c1]

COB-203

COB-203 was prepared from COB-197 according to Synthetic Example 3 on a 0.27-mmol scale. Based on 84 mg of product recovered, the yield was 90%. For the COB-203, the following data were obtained: $R_f$ 0.32 (60% EtOAc in hexanes); $t_R$=4.13 min (LCMS); $^1$H NMR (CDCl$_3$, 300 MHz) δ 8.33 (d, 1H, Ar), 7.91 (s, 1H, Ar), 7.41 (d, 1H, Ar), 7.08-7.04 (m, 1H, Ar), 6.93-6.89 (in, 1H, Ar), 6.79 (d, 1H, Ar), 6.39-6.38 (m, 2H, Ar and CH), 5.26 (s, 2H, CH$_2$), 3.58 (s, 3H, OMe), 3.22 (s, 3H, OMe).

Example 37

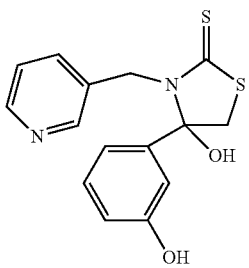 [SMILES: Oc1cccc(C2(O)CSC(=S)N2Cc2cccnc2)c1]

COB-198

COB-198 was prepared according to Synthetic Example 2 on a 1.5-mmol scale. Based on 69.9 mg of product recovered, the yield was 22%. For the COB-198, the following data were obtained: $R_f$ 0.3 (60% EtOAc in hexanes); $t_R$=5.49 min; $^1$H NMR (DMSO-d$_6$, 300 MHz) δ 8.37-8.35 (m, 2H, Ar and ArOH), 7.82 (s, 1H, OH), 7.63-7.60 (m, 1H, Ar), 7.27-7.13 (m, 3H, Ar), 6.826.71 (m, 3H, Ar), 4.85 (d, J=15.3 Hz, 1H, NCHH), 4.43 (d, J=15.3 Hz, 1H, NCHH), the SCH$_2$ peaks overlap with the water peak. The compound was not pure after three purifications according to HPLC (89% purity).

Example 38

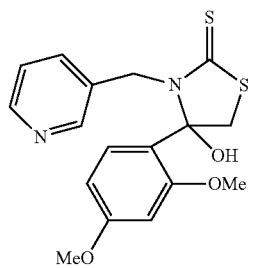 [SMILES: COc1ccc(C2(O)CSC(=S)N2Cc2cccnc2)c(OC)c1]

COB-199

COB-199 was prepared according to Synthetic Example 2 on a 1.5-mmol scale. Based on 203 mg of product recovered, the yield was 56%. For the COB-199, the following data were obtained: $R_f$ 0.3 (60% EtOAc in hexanes); $t_R$=3.39 min (LCMS); $^1$H NMR (DMSO-d$_6$, 300 MHz) δ 8.25 (dd, 1H, Ar), 8.07 (d, 1H, Ar), 7.73 (s, 1H, OH), 7.56 (d, 1H, Ar), 7.40 (dt, 1H, Ar), 7.12-7.07 (m, 1H, Ar), 6.53 (dd, 1H, Ar), 6.08 (d, 1H, Ar), 4.91 (d, J=15.3 Hz, 1H, NCHH), 4.31 (d, J=15.3 Hz, 1H, NCHH), 3.83 (d, J=12 Hz, 1H, SCHH), 3.71 (s, 3H, OCH$_3$), 3.43 (s, 3H, OCH$_3$), 3.25 (d, J=12 Hz, 1H, SCHH); $^{13}$C NMR (DMSO-d$_6$, 75 MHz) δ 196.0, 161.5, 157.1, 135.4, 132.4, 122.3, 119.9, 109.9, 97.6, 55.3, 40.3.

Example 39

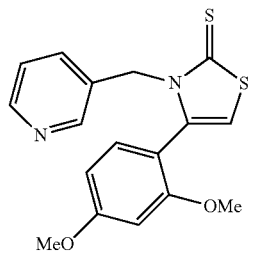 [SMILES: COc1ccc(-c2csc(=S)n2Cc2cccnc2)c(OC)c1]

COB-204

COB-204 was prepared from COB-199 according to Synthetic Example 3 on a 0.28-mmol scale. Based on 81 mg of product recovered, the yield was 87%. For the COB-204, the following data were obtained: $R_f$ 0.32 (60% EtOAc in hexanes); $t_R$=4.03 min (LCMS); $^1$H NMR (CDCl$_3$, 300 MHz) δ 8.40 (d, 1H, Ar), 7.99 (s, 1H, Ar), 7.53 (d, 1H, Ar), 7.28-7.11 (m, 1H, Ar), 6.85 (d, 1H, Ar), 6.456.41 (m, 3H, Ar and CH), 5.29 (s, 2H, CH$_2$), 3.82 (s, 3H, OMe), 3.59 (s, 3H, OMe).

Example 40

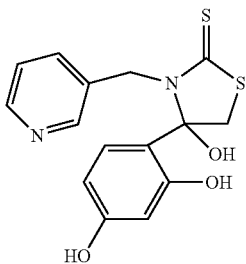 [SMILES: Oc1ccc(C2(O)CSC(=S)N2Cc2cccnc2)c(O)c1]

COB-200

COB-200 was prepared according to Synthetic Example 2 on a 1.5-mmol scale. Based on 131 mg of product recovered, the yield was 40%. For the COB-200, the following data were obtained: $R_f$ 0.11 (60% EtOAc in hexanes); $t_R$=2.75 min (LCMS); $^1$H and $^{13}$C NMR were not optimal, but based on the LCMS (96.9%), the compound was considered clean enough to be sent for tests.

Example 41

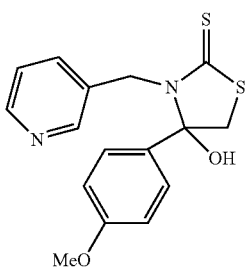 [SMILES: COc1ccc(C2(O)CSC(=S)N2Cc2cccnc2)cc1]

COB-201

COB-201 was prepared according to Synthetic Example 2 on a 1.6-mmol scale. Based on 153 mg of product recovered, the yield was 46%. For the COB-201, the following data were obtained: $R_f$ 0.28 (60% EtOAc in hexanes); $t_R$=3.56 min (LCMS); $^1$H NMR (DMSO-$d_6$, 300 MHz) δ 8.36-8.35 (m, 2H, Ar), 7.75 (s, 1H, OH), 7.58 (d, 1H, Ar), 7.32-7.21 (m, 3H, Ar), 6.89 (d, 2H, Ar), 4.77 (d, J=15.4 Hz, 1H, NCHH), 4.52 (d, J=15.4 Hz, 1H, NCHH), 3.373.68 (m, 5H, SCH$_2$ and OCH$_3$); $^{13}$C NMR (DMSO-$d_6$, 75 MHz) δ 195.6, 159.5, 148.9, 147.7, 135.3, 132.4, 132.35, 127.0, 122.8, 113.7, 100.1, 55.2, 46.9, 42.5.

Example 42

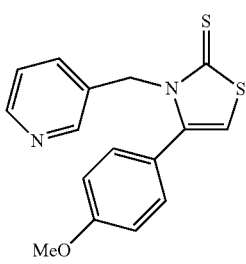 [SMILES: COc1ccc(-c2csc(=S)n2Cc2cccnc2)cc1]

COB-206

COB-206 was prepared from COB-201 according to Synthetic Example 3 on a 0.18-mmol scale. Based on 39 mg of product recovered, the yield was 69%. For the COB-206, the following data were obtained: $R_f$ 0.26 (60% EtOAc in hexanes); $t_R$=4.15 min (LCMS); $^1$H NMR (CDCl$_3$, 300 MHz) δ 8.40 (d, 1H, Ar), 8.0 (s, 1H, Ar), 7.43 (d, 1H, Ar), 7.13-7.08 (m, 1H, Ar), 6.95 (d, 2H, Ar), 6.82 (d, 2H, Ar), 6.39 (s, 1H, CH), 5.35 (s, 2H, CH$_2$), 3.76 (s, 3H, OMe).

Example 43

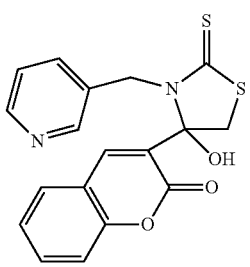

COB-202

COB-202 was prepared according to Synthetic Example 2 on a 1.5-mmol scale. Based on 114 mg of product recovered, the yield was 35%. For the COB-202, the following data were obtained: $R_f$ 0.22 (60% EtOAc in hexanes); $t_R$=3.12 min (LCMS); $^1$H NMR (DMSO-$d_6$, 300 MHz) δ 8.41 (s, 1H, OH), 8.28-8.23 (m, 3H, Ar), 7.87 (dd, 1H, Ar), 7.66-7.56 (m, 2H, Ar), 7.41-7.36 (td, 1H, Ar), 7.28 (d, 1H, Ar), 7.08 (dd, 1H, CH), 5.08 (d, J=15.5 Hz, 1H, NCHH), 4.56 (d, J=15.5 Hz, 1H, NCHH), 3.98 (d, J=12.3 Hz, 1H, SCHH), 3.28 (d, J=12.3 Hz, 1H, SCHH) this signal overlaps with the signal for water; $^{13}$C NMR was recorded, but the signal was weak such that only six carbon are observed.

Example 44

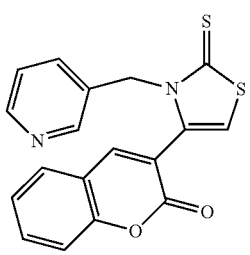 [SMILES: O=c1oc2ccccc2cc1-c1csc(=S)n1Cc1cccnc1]

COB-205

COB-205 was prepared from COB-202 according to Synthetic Example 3 on a 0.13-mmol scale. Based on 33.4 mg of product recovered, the yield was 70%. For the COB-205, the following data were obtained: $R_f$ 0.25 (60% EtOAc in hexanes); $t_R$=3.46 min (LCMS); $^1$H NMR (CDCl$_3$, 300 MHz) δ 8.34 (s, 1H, Ar), 8.20 (s, 1H, Ar), 7.59-7.43 (m, 2H, Ar), 7.34 (s, 1H, Ar), 7.33-7.30 (m, 2H, Ar), 7.25-7.06 (m, 1H, Ar), 6.59 (s, 1H, CH), 5.51 (s, 2H, CH$_2$).

Example 45

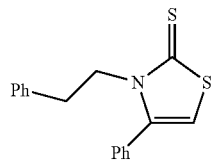
COB-177

COB-177 was prepared according to Synthetic Example 3 on a 0.124-mmol scale by dehydrating the reaction product of 2-bromo-1-phenylethanone and 2-phenylethanamine formed according to Synthetic Example 2. Based on 28 mg of product recovered, the yield was 88%. For the COB-177, the following data were obtained: $R_f$ 0.6 (5% EtOAc in toluene); $t_R$=17.08 min; $^1$H NMR (CDCl$_3$, 300 MHz) δ 7.53-7.43 (m, 3H, Ar), 7.21-7.17 (m, 5H, Ar), 6.96-6.93 (m, 2H, Ar), 6.45 (s, 1H, CH), 4.36-4.30 (m, 2H, NCH$_2$), 2.98 (t, =7.95 Hz, 2H, PhCH$_2$); $^{13}$C NMR. (CDCl$_3$, 75 MHz) δ 188.1, 144.9, 137.6, 130.9, 130.1, 129.7, 129.1, 129.0, 128.8, 126.9, 109.0, 49.4, 33.4.

Example 46

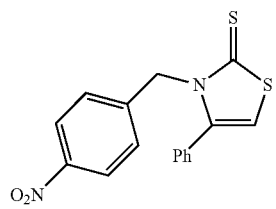
COB-191

COB-191 was prepared according to Synthetic Example 3 on a 0.25-mmol scale by dehydrating the reaction product of 2-bromo-1-phenylethanone and 1-(4-nitrophenyl)methanamine formed according to Synthetic Example 2. Based on 77.9 mg of product recovered, the yield was 89%. For the COB-191, the following data were obtained: $R_f$ 0.37 (20% EtOAc in hexanes); $t_R$=15.78 min; $^1$H NMR (CDCl$_3$, 300 MHz) δ 8.10 (d, 2H, Ar), 7.48-7.46 (m, 1H, Ar), 7.41; 7.35 (m, 2H, Ar), 7.14-7.10 (m, 4H, Ar), 6.56 (s, 1H, CH), 5.51 (s, 2H, NCH$_2$), 3.77 (s, 3H, OCH$_3$); $^{13}$C NMR (CDCl$_3$, 75 MHz) δ 189.9, 147.6, 144.6, 142.8, 130.5, 129.6, 129.3, 128.2, 124.0, 109.5, 50.4.

Example 47

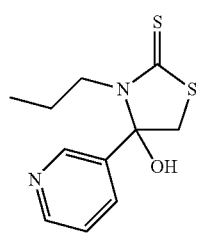 [SMILES: CCCN1C(=S)SCC1(O)c1cccnc1]
COB-207

COB-207 may be prepared according to Synthetic Example 2.

Example 48

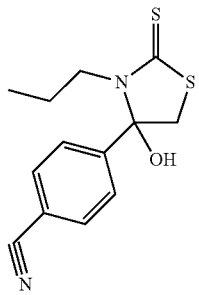 [SMILES: CCCN1C(=S)SCC1(O)c1ccc(C#N)cc1]
COB-208

COB-208 may be prepared according to Synthetic Example 2.

Example 49

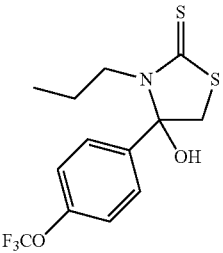 [SMILES: CCCN1C(=S)SCC1(O)c1ccc(OC(F)(F)F)cc1]
COB-209

COB-209 may be prepared according to Synthetic Example 2.

Example 50

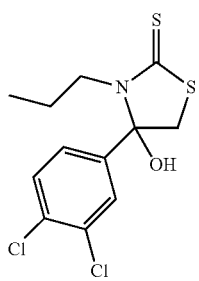 [SMILES: CCCN1C(=S)SCC1(O)c1ccc(Cl)c(Cl)c1]
COB-210

COB-210 may be prepared according to Synthetic Example 2.

Example 51

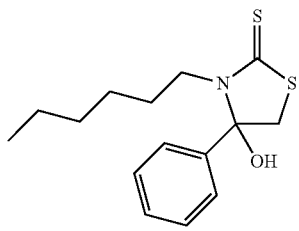 [SMILES: CCCCCCN1C(=S)SCC1(O)c1ccccc1]
COB-212

COB-212 may be prepared according to Synthetic Example 2.

Example 52

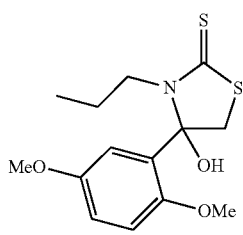 [SMILES: CCCN1C(=S)SCC1(O)c1cc(OC)ccc1OC]
COB-213

COB-213 may be prepared according to Synthetic Example 2.

Example 53

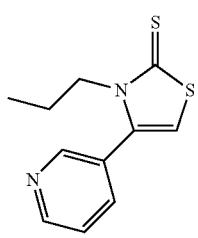
COB-214

COB-214 may be prepared according to Synthetic Example 3.

Example 54

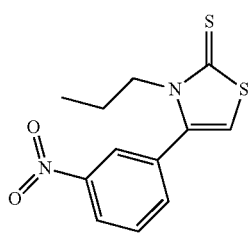
COB-215

COB-215 may be prepared according to Synthetic Example 3.

Example 55

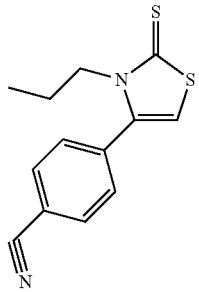
COB-216

COB-216 may be prepared according to Synthetic Example 3.

Example 56

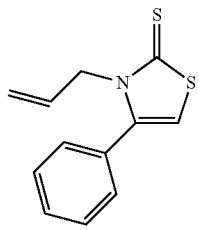
COB-217

COB-217 may be prepared according to Synthetic Example 3.

Example 57

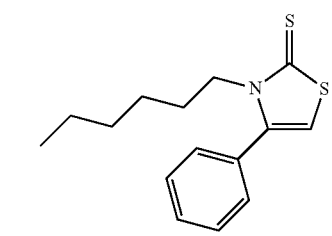 [SMILES: CCCCCCn1c(-c2ccccc2)csc1=S]
COB-218

COB-218 may be prepared according to Synthetic Example 3.

Example 58

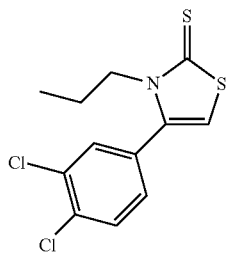
COB-219

COB-219 may be prepared according to Synthetic Example 3.

Example 59

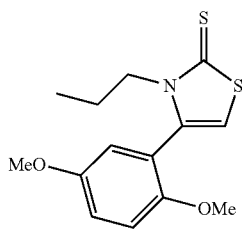
COB-220

COB-220 may be prepared according to Synthetic Example 3.

Example 60

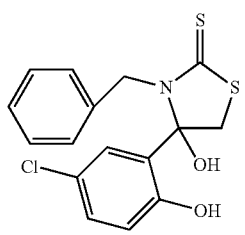 [SMILES: Oc1ccc(Cl)cc1C1(O)CSC(=S)N1Cc1ccccc1]
COB-221

COB-221 may be prepared according to Synthetic Example 2.

Example 61

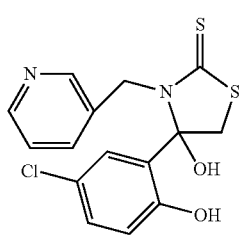 [SMILES: Oc1ccc(Cl)cc1C1(O)CSC(=S)N1Cc1cccnc1]
COB-222

COB-222 may be prepared according to Synthetic Example 2.

Example 62

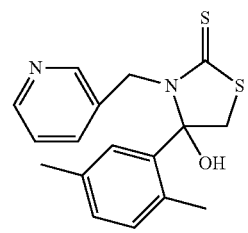 [SMILES: Cc1ccc(C)c(C2(O)CSC(=S)N2Cc2cccnc2)c1]
COB-223

COB-223 may be prepared according to Synthetic Example 2.

Example 63

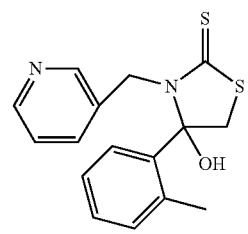 [SMILES: Cc1ccccc1C1(O)CSC(=S)N1Cc1cccnc1]
COB-224

COB-224 may be prepared according to Synthetic Example 2.

Example 64

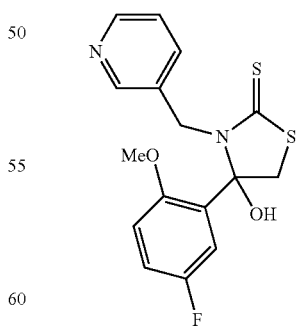
COB-225

COB-225 may be prepared according to Synthetic Example 2.

Example 65

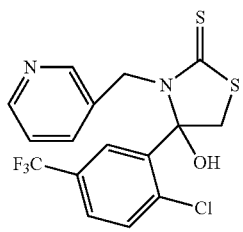 [SMILES: OC1(c2cc(C(F)(F)F)ccc2Cl)CSC(=S)N1Cc1cccnc1]

COB-226

COB-226 may be prepared according to Synthetic Example 2.

Example 66

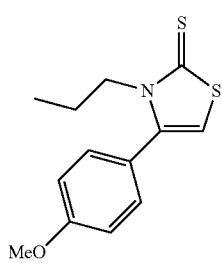 [SMILES: CCCn1c(-c2ccc(OC)cc2)csc1=S]

DRB-3

DRB-3 may be prepared according to Synthetic Example 3.

Example 67

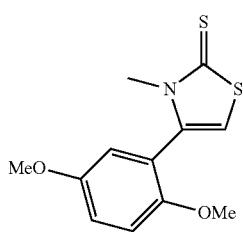 [SMILES: COc1ccc(OC)c(-c2csc(=S)n2C)c1]

GWB-93

GWB-93 may be prepared according to Synthetic Example 3.

Example 68

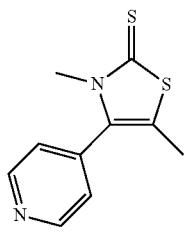

Z-01

Z-01 may be prepared according to Synthetic Example 3.

Example 69

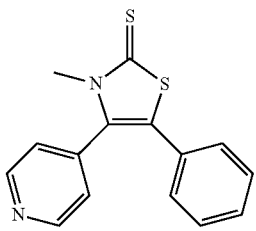 [SMILES: Cn1c(-c2ccncc2)c(-c2ccccc2)sc1=S]

Z-02

Z-02 may be prepared according to Synthetic Example 3.

Example 70

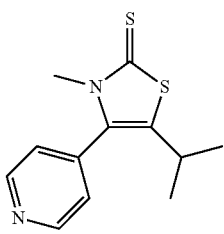 [SMILES: CC(C)c1sc(=S)n(C)c1-c1ccncc1]

Z-03

Z-03 may be prepared according to Synthetic Example 3.

Example 71

Z-04

Z-04 may be prepared according to Synthetic Example 3.

Example 72

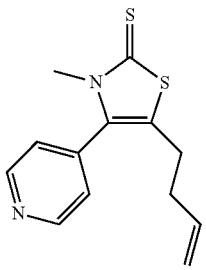

Z-05

Z-05 may be prepared according to Synthetic Example 3.

Example 73

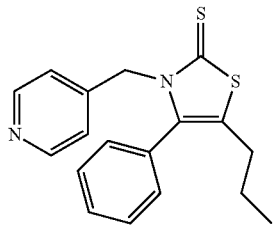

Z-06

Z-06 may be prepared according to Synthetic Example 3.

Example 74

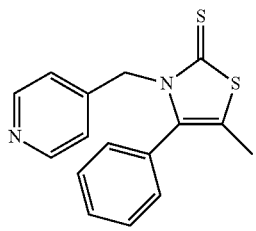

Z-07

Z-07 may be prepared according to Synthetic Example 3.

Example 75

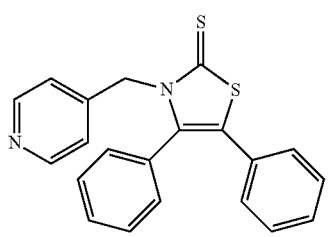

Z-08

Z-08 may be prepared according to Synthetic Example 3.

Example 76

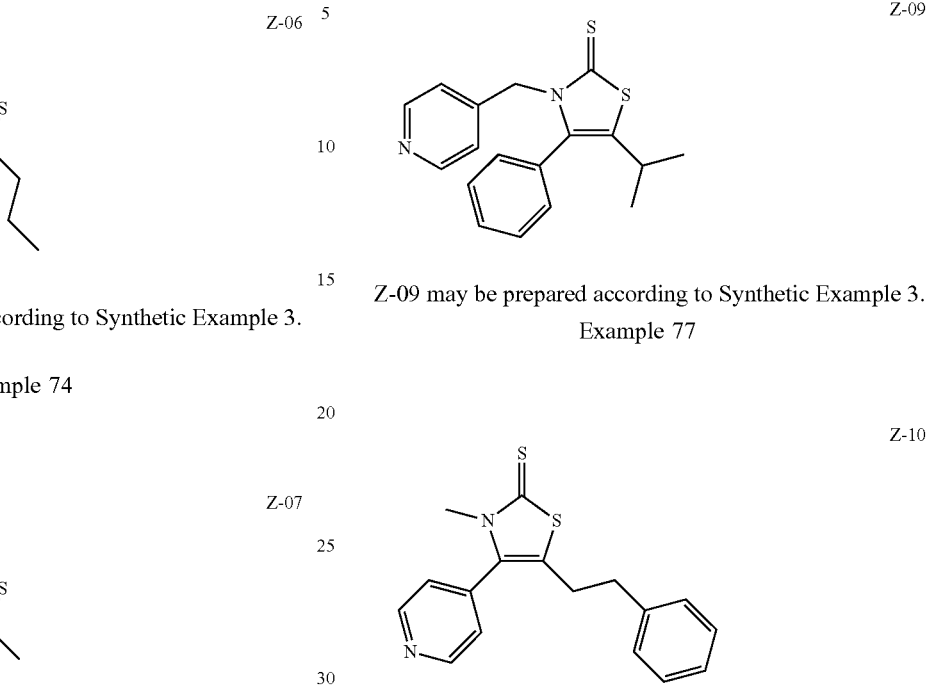

Z-09 may be prepared according to Synthetic Example 3.

Example 77

Z-10 may be prepared according to Synthetic Example 3.

Characterizations of Signal Modification

Murine macrophages were treated with LPS in the presence of various exemplary compounds described above. Subsequently, the cells were harvested and the transcripts for IL-6, iNOS, and INF-β quantified via rt-PCR. $IC_{50}$ is the concentration of the compounds required to inhibit 50% of the mRNA transcripts induced by LPS. $TC_{50}$ is the concentration of the compounds required to diminish the MTS signal by 50% (MTS signal correlates with cell metabolism/viability). Therapeutic Index (TI) is the ratio of $TC_{50}$ to $IC_{50}$.

In TABLE 4, data are provided that show effects of exemplary compounds described above on the inhibition of LPS induction of IL-6, iNOS, and INF-β transcripts in macrophages. The IL-6, iNOS, and INF-β transcripts are key mediators in a plethora of signaling networks that are involved in normal physiology and pathological processes. The mechanism by which LPS induces the IL-6, iNOS, and INF-β transcripts is via a network of signaling events. Thus, in these examples, the compounds inhibit signaling processes that lead to the induction of other molecules which themselves are signaling molecules. Data in TABLE 4 that was not calculatable is noted "NC."

TABLE 4

| Compound | Average $IC_{50}$ (μm) | | | Average $TC_{50}$ (μm) | Average Therapeutic Index (TI) | | |
|---|---|---|---|---|---|---|---|
| | IL-6 | iNOS | INF-β | | IL-6 | iNOS | INF-β |
| COB-117 | 30 | 36 | 22 | — | — | — | — |
| COB-119 | 45 | 60 | 46 | 390 | 8.7 | 6.5 | 8.5 |
| COB-123 | 19 | 55 | 21 | — | — | — | — |
| COB-125 | 31 | 43 | 36 | 500 | 16.1 | 11.6 | 13.9 |
| COB-130 | 29 | 26 | 47 | — | — | — | — |
| COB-132 | 26 | 38 | 85 | 360 | 13.8 | 9.5 | 4.2 |
| COB-134 | 66 | 87 | 135 | — | — | — | — |

TABLE 4-continued

| Compound | Average IC$_{50}$ (μm) | | | Average TC$_{50}$ (μm) | Average Therapeutic Index (TI) | | |
|---|---|---|---|---|---|---|---|
| | IL-6 | iNOS | INF-β | | IL-6 | iNOS | INF-β |
| COB-143 | 13 | 3 | 1 | 23 | 1.8 | 7.7 | 23.0 |
| COB-152 | 4.25 | 0.156 | 0.156 | 18 | 4.2 | 115.4 | 115.4 |
| COB-168 | 17 | 1.5 | 1.5 | 12 | 0.7 | 8.0 | 8.0 |
| COB-177 | 8 | 32 | 13 | NC | — | — | — |
| COB-183 | 19 | 9.5 | 8 | >50 | >2.6 | >5.3 | >6.3 |
| COB-186 | <30% (0.03 μM-2 μM) | 1.9 | 40% (0.5 μM-2 μM) | 4 | — | — | — |
| COB-187 | NC | 0.375 | 0.125 | 15 | NC | 40.0 | 120.0 |
| COB-188 | NC | 0.25 | 0.25 | 13 | NC | 52.0 | 52.0 |
| COB-196 | NC | 0.5 | 0.375 | 17 | NC | 34.0 | 45.3 |
| COB-197 | NC | 2.5 | 2.5 | NC | — | — | — |
| COB-198 | NC | 0.15 | 0.2 | 17 | NC | 113.3 | 85.0 |
| COB-199 | NC | 2.2 | >5 | 23 | NC | 10.5 | >4.5 |
| COB-200 | NC | 0.5 | 0.4 | 11 | NC | 22.0 | 27.5 |
| COB-201 | NC | 0.45 | 1.25 | 10 | NC | 22.2 | 8.0 |
| COB-202 | NC | 2.2 | 4.4 | 43 | NC | 19.5 | 9.8 |
| COB-203 | 19.5 | NC | 8 | 270 | 13.8 | NC | 33.8 |
| COB-204 | 5 | 7 | 14 | 130 | 26.0 | 18.6 | 9.3 |
| COB-206 | 10.5 | 54 | 30 | 120 | 11.4 | 2.2 | 4.0 |
| COB-207 | 12 | 2.7 | 2.1 | — | — | — | — |
| COB-210 | 16 | 2 | 3 | 45 | 2.8 | 22.5 | 15.0 |
| COB-212 | NC | 3.4 | 3.6 | 54 | NC | 15.9 | 15.0 |
| COB-214 | 6 | 10.5 | — | 230 | 38.0 | 22.0 | — |
| COB-215 | 8.8 | ~10 | ~10 | ~100 | ~11.5 | ~10 | ~10 |
| COB-216 | 8.1 | ~10 | ~10 | >100 | ~12 | ~10 | ~10 |
| COB-217 | 8.2 | ~10 | ~10 | 30% (100 μM) | — | — | — |
| COB-218 | 9.5 | NC | 10.5 | 0% (100 μM) | — | — | — |
| COB-219 | 8.5 | ~20 | 16.5 | 30% (100 μM) | — | — | — |
| COB-220 | 5.5 | 3.75 | 12.25 | 60 | 10.9 | 16.0 | 4.9 |
| COB-221 | >10 | 1.8 | 1.5 | 18 | >1.8 | 10.0 | 12.0 |
| COB-222 | 8.6 | 0.45 | 0.45 | 15 | 1.7 | 33.3 | 33.3 |
| COB-223 | 3.5 | 0.4 | 0.4 | 14 | 4.0 | 35.0 | 35.0 |
| COB-224 | 3.5 | 0.4 | 0.45 | 13 | 3.7 | 32.5 | 28.9 |
| COB-225 | 32.5 | 1 | 1 | 65 | 2.0 | 65.0 | 65.0 |
| COB-226 | 12.5 | 1.5 | 1.5 | 33 | 2.6 | 22.0 | 22.0 |

From the above table, it is apparent that these compounds are highly potent, in some cases achieving an IC$_{50}$ in the nM range. This inhibition is not due to cell death. For example, in certain cases the concentration of the compound required to diminish the MTS signal by 50% (MTS signal correlates with cell metabolism/viability), i.e. the TC$_{50}$, was over 100 times greater than the IC$_{50}$.

In the above examples, the mode of initiation of the signaling network was treatment with LPS. The modification of signaling is not unique to this mode of initiation of the signaling. For example, these compounds may also modify signaling initiated by TNF-α.

It is surprising that these compounds achieve such a high level of potency in terms of their ability to modify signaling processes, yet in many cases have little effect on the viability of the cells.

Preparation of Pharmaceutical Compositions
Composition Administration

Means of administering active compounds according to embodiments herein include, but are not limited to, oral, sublingual, intravenous, intramuscular, intraperitoneal, percutaneous, intranasal, intrathecal, subcutaneous, or enteral. Local administration to the afflicted site may be accomplished through means known in the art, including, but not limited to, topical application, injection, infusion and implantation of a porous device in which the active compound(s) or compositions described herein are contained. Accordingly, the active compounds described herein will generally be administered as a pharmaceutical composition comprising one or more active compounds described herein in combination with a pharmaceutically acceptable excipient and other formulational aids.

Formulational Aids

Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Alternatively, one may incorporate or encapsulate the active compounds described herein in a suitable polymer matrix or membrane, thus providing a sustained-release device suitable for implantation near the site to be treated locally. Other devices include indwelling catheters and devices such as the Alzet® minipump. Opthalmic preparations may be formulated using commercially available vehicles such as Sorbi-care® (Allergan), Neodecdron® (Merck, Sharp & Dohme), Lacrilube®, and the like. Further, one may provide the active compounds described herein in bulking agents, for example human serum albumin, sucrose, mannitol, and the like. A thorough discussion of pharmaceutically acceptable excipients is available in Remington's Pharmaceutical Sciences I (Mack Pub. Co.), incorporated herein by reference.

Oral/Parenteral Administration

The active compounds and pharmaceutical compositions according to embodiments herein can be administered both orally and parenterally in accordance with conventional procedures for the treatment of autoimmune disease and performance of organ and/or tissue transplantation. The amount of active compound required to treat any particular autoimmune and/or transplant disorder will, of course, vary depending upon the nature and severity of the disorder, the age and condition of the subject, and other factors readily determined by one of ordinary skill in the art. Active compounds are administered in dosage units, preferably divided dosage units, containing the active compound with a suitable physiologically acceptable carrier or excipient, many of which are well known to those in the art and are described above. The dosage units can be in the form of a liquid preparation, e.g., solutions, suspensions, dispersions, or emulsions, or they may be in solid form such as pills, tablets, capsules or the like. Compositions in unit dosage form, i.e., pharmaceutical compositions which are available in a pre-measured form suitable for single dose administration without requiring that the individual dosage be measured out by the user, for example, pills, tablets, capsules, or ampules are particularly preferred methods of administration of the active compounds described herein.

Specific/Preferred Indications

For the treatment of autoimmune and transplantation disorders pharmaceutical compositions in dosage unit form comprise an amount of composition which provides from about 0.05 mg to about 60 mg, preferably from about 0.05 mg to about 20 mg, of active compound per day. To produce dosage units for peroral administration, the active compound according to embodiments herein or a salt thereof is combined, e.g., with solid powdered carriers such as lactose, sucrose, mannitol; starches such as potato starch, corn starch or amylopectin, as well as laminaria powder and citrus pulp powder; cellulose derivatives of gelatin, also lubricants such as magnesium or calcium sterate of polyethylene glycols (carbowaxes) of suitable molecular weights may be added, to form compressed tablets or core tablets for sugar coating. The latter are coated, for example, with concentrated sugar solutions which, e.g., can contain gum arabic, talcum and/or titanium dioxide, or they are coated with a lacquer dissolved in easily volatile organic solvents or mixture of organic solvents. Dyestuffs can be added to these coatings, for example, to distinguish between different contents of active substance. Capsules useful herein include, for example, soft gelatin capsules (pearl-shaped closed capsules), geltabs, other capsules which consist, for example, of a mixture of gelatin and glycerin and contain, e.g., mixtures of the active substances or a suitable salt thereof with solid, powdered carriers such as, e.g., lactose, sucrose, sorbital, mannitol; starches such as potato starch corn starch or amylopectin, cellulose derivatives or gelatin, as well as magnesium sterate or steric acid. Suppositories are employed as dosage units for rectal application. These consist of a combination of the active substance or a suitable salt thereof with a neutral fatty base, or also gelatin rectal capsules can be employed which consist of a combination of the active substance or a suitable salt thereof with polyethylene glycols (carbowaxes) of suitable molecular weight.

Ampoules for parenteral administration, particularly intramuscular administration, preferably contain an active compound or a water soluble salt thereof and suitable stabilizing agents, and, if necessary, buffer substances in aqueous solution. Anti-oxidizing agents such as sodium bisulfite, sodium sulfite, ascorbic acid or Rongalit (formaldehyde-sodium bisulfite compound), and the like are suitable as stabilizing agents either alone or combined, in total concentrations from about 0.01% to about 0.05% by weight of the composition. Because of its ability to form chelates, ascorbic acid has an additional stabilizing effect; in this function it can also be replaced by other chelate-formers. The best suitability of the active ingredient is attained, e.g., by mixtures in suitable ratio of sodium sulfite, sodium bisulfite and/or ascorbic acid, or by the addition of other buffer substances such as citric acid and/or salts thereof. In addition, the ampoules can contain a slight amount of a preservative.

Useful pharmaceutical formulations for administration of the active compounds according to embodiments herein may be illustrated below. They are made using conventional techniques.

Capsules
Active ingredient 0.05 to 20 mg
Lactose 20-100 mg
Corn Starch U.S.P. 20-100 mg
Aerosolized silica gel 2-4 mg
Magnesium stearate 1-2 mg Tablets
Active ingredient 0.05 to 20 mg
Microcrystalline cellulose 50 mg
Corn Starch U.S.P. 80 mg
Lactose U.S.P. 50 mg
Magnesium stearate U.S.P. 1-2 mg The tablets can be sugar coated according to conventional art practices. Colors may be added to the coating.

Chewable Tablets
Active ingredient 0.05 to 20 mg
Mannitol, N.F. 100 mg
Flavor 1 mg
Magnesium stearate U.S.P. 2 mg Suppositories
Active ingredient 0.05 to 20 mg
Suppository base 1900 mg Liquid
Active ingredient 2.0 percent
Polyethylene glycol 300, N.F. 10.0 percent
Glycerin 5.0 percent
Sodium bisulfite 0.02 percent
Sorbitol solution 70%, U.S.P. 50 percent
Methylparaben, U.S.P. 0.1 percent
Propylparaben, U.S.P. 0.2 percent
Distilled water, U.S.P. (q.s.) 100.0 cc Injectable
Active ingredient 0.05 to 60 mg
Polyethylene glycol 600 1.0 cc
Sodium bisulfite, U.S.P. 0.4 mg
Water for injection, U.S.P. (q.s.) 2.0 cc Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the appended claims or to imply that certain features are critical, essential, or important to the structure or function of the claimed subject matter. Rather, these terms are merely intended to highlight alternative or additional features that may or may not be utilized in a particular embodiment.

What is claimed is:

1. A composition comprising at least one compound having General Formula (I) or General Formula (II):

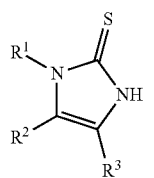

(I)

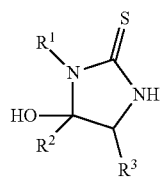

(II)

or a pharmaceutically-acceptable salt or solvate thereof, in which:

$R^1$ is methyl;

$R^2$ is selected from the group consisting of $Q^2$,

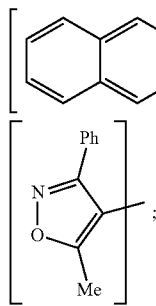

$Q^2$ is

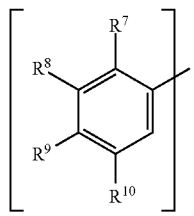

where exactly two or exactly three of $R^7$, $R^8$, $R^9$, and $R^{10}$ are hydrogen and the remaining two or one of $R^7$, $R^8$, $R^9$, and $R^{10}$ are independently, selected from the group consisting of methoxy, ethoxy, hydroxy, trifluoromethoxy, N-methylamino, (N,N)-dimethylamino, cyano, chloro, fluoro, and nitro, provided $Q^2$ is not 4-methoxyphenyl, 4-chlorophenyl, 4-fluorophenyl, 4-hydroxyphenyl, 3,4-dichlorophenyl, or 3-nitrophenyl; and $R^3$ is selected from the group consisting of hydrogen, methyl, ethyl, n-propyl, isopropyl, butyl, 4-butenyl, phenyl, and 2-phenylethyl.

2. The composition of claim 1, wherein $R^2$ is a group $Q^2$.

3. The composition of claim 1, wherein $R^2$ is a group $Q^2$ selected from the group consisting of 2-methoxyphenyl, 3-methoxyphenyl, 3-chlorophenyl, 2,5-dimethoxyphenyl, 2,4-dimethoxyphenyl, 3,4-dimethoxyphenyl, 2,4-dichlorophenyl, 2,4-difluorophenyl, 4-(dimethylamino)phenyl, 4-(trifluoromethoxy)phenyl, 4-cyanophenyl, 3-hydroxyphenyl, 2,4-dihydroxyphenyl, 2-hydroxy-5-chlorophenyl, and 2-methoxy-5-fluorophenyl.

4. The composition of claim 1, wherein $R^2$ is a group $Q^2$ selected from the group consisting of 2-methoxyphenyl, 3-methoxyphenyl, 3-chlorophenyl, 2,5-dimethoxyphenyl, 2,4-dimethoxyphenyl, 3,4-dimethoxyphenyl, 2,4-dichlorophenyl, 2,4-difluorophenyl, 4-(dimethylamino)phenyl, 4-(trifluoromethoxy)phenyl, and 4-cyanophenyl.

5. The composition of claim 1, wherein $R^2$ is a group $Q^2$ selected from the group consisting of 3-methoxyphenyl, 3-chlorophenyl, 2,5-dimethoxyphenyl, 2,4-dimethoxyphenyl, 3,4-dimethoxyphenyl, and 4-(trifluoromethoxy)phenyl.

6. The composition of claim 1, wherein $R^2$ is a group $Q^2$ selected from the group consisting of 2,4-dimethoxyphenyl, 2,5-dimethoxyphenyl, and 3,4-dimethoxyphenyl.

7. A composition comprising at least one compound having General Formula (I):

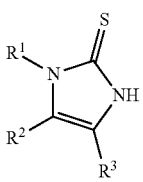

(I)

or a pharmaceutically-acceptable salt or solvate thereof, in which:

$R^1$ is methyl;

$R^2$ is selected from the group consisting of $Q^2$,

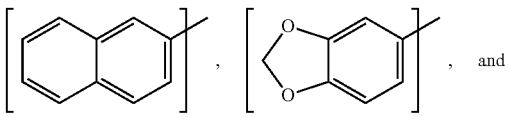

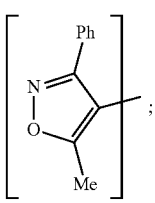

Q² is

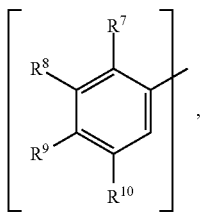

where exactly two or exactly three of R⁷, R⁸, R⁹, and R¹⁰ are hydrogen and the remaining two or one of R⁷, R⁸, R⁹, and R¹⁰ are independently selected from the group consisting of methoxy, ethoxy, hydroxy, trifluoromethoxy, N-methylamino, (N,N)-dimethylamino, cyano, chloro, fluoro, and nitro, provided Q² is not 4-methoxyphenyl, 4-chlorophenyl, 4-fluorophenyl, 4-hydroxyphenyl, 3,4-dichlorophenyl, or 3-nitrophenyl; and R³ is hydrogen.

8. The composition of claim 7, wherein R² is a group Q².

9. The composition of claim 7, wherein R² is a group Q² selected from the group consisting of 2-methoxyphenyl, 3-methoxyphenyl, 3-chlorophenyl, 2,5-dimethoxyphenyl, 2,4-dimethoxyphenyl, 3,4-dimethoxyphenyl, 2,4-dichlorophenyl, 2,4-difluorophenyl, 4-(dimethylamino)phenyl, 4-(trifluoromethoxy)phenyl, 4-cyanophenyl, 3-hydroxyphenyl, 2,4-dihydroxyphenyl, 2-hydroxy-5-chlorophenyl, and 2-methoxy-5-fluorophenyl.

10. The composition of claim 7, wherein R² is a group Q² selected from the group consisting of 2,5-dimethoxyphenyl, 2,4-dimethoxyphenyl, 3,4-dimethoxyphenyl, 2,4-dichlorophenyl, 2,4-difluorophenyl, 2,4-dihydroxyphenyl, 2-hydroxy-5-chlorophenyl, and 2-methoxy-5-fluorophenyl.

11. The composition of claim 7, wherein R² is a group Q² selected from the group consisting of 2-methoxyphenyl, 3-methoxyphenyl, 3-chlorophenyl, 2,5-dimethoxyphenyl, 2,4-dimethoxyphenyl, 3,4-dimethoxyphenyl, 2,4-dichlorophenyl, 2,4-difluorophenyl, 4-(dimethylamino)phenyl, 4-(trifluoromethoxy)phenyl, and 4-cyanophenyl.

12. The composition of claim 7, wherein R² is a group Q² selected from the group consisting of 3-methoxyphenyl, 3-chlorophenyl, 2,5-dimethoxyphenyl, 2,4-dimethoxyphenyl, 3,4-dimethoxyphenyl, and 4-(trifluoromethoxy)phenyl.

13. The composition of claim 7, wherein R² is a group Q² selected from the group consisting of 2,4-dimethoxyphenyl, 2,5-dimethoxyphenyl, and 3,4-dimethoxyphenyl.

14. The composition of claim 7, wherein R² is selected from the group consisting of

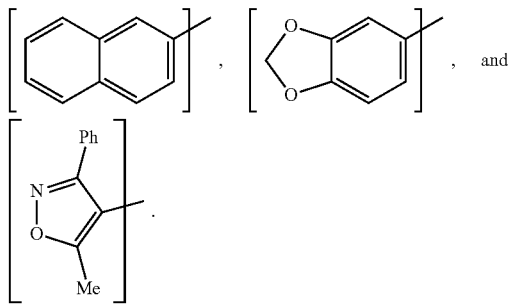

\* \* \* \* \*